(12) United States Patent
Parker et al.

(10) Patent No.: US 6,827,456 B2
(45) Date of Patent: Dec. 7, 2004

(54) TRANSREFLECTORS, TRANSREFLECTOR SYSTEMS AND DISPLAYS AND METHODS OF MAKING TRANSREFLECTORS

(75) Inventors: Jeffery R. Parker, Richfield, OH (US); Timothy A. McCollum, Westlake, OH (US)

(73) Assignee: Solid State Opto Limited (VG)

( * ) Notice: Subject to any disclaimer, the term of this patent is extended or adjusted under 35 U.S.C. 154(b) by 0 days.

(21) Appl. No.: 10/010,835

(22) Filed: Dec. 5, 2001

(65) Prior Publication Data

US 2002/0080598 A1 Jun. 27, 2002

Related U.S. Application Data

(63) Continuation-in-part of application No. 09/256,275, filed on Feb. 23, 1999, now Pat. No. 6,712,481.

(51) Int. Cl.[7] .............................................. F21V 7/04
(52) U.S. Cl. ...................... 362/31; 362/339; 362/330
(58) Field of Search ........................... 362/26, 31, 330, 362/339

(56) References Cited

U.S. PATENT DOCUMENTS 5,377,084 A * 12/1994 Kojima et al. ................ 362/31
5,598,280 A * 1/1997 Nishio et al. .................. 349/57
5,851,062 A * 12/1998 Shinohara et al. ............ 362/31
5,971,559 A    10/1999 Ishikawa et al.

* cited by examiner

Primary Examiner—Thomas M. Sember
(74) Attorney, Agent, or Firm—Renner, Otto, Boisselle & Sklar, LLP

(57) ABSTRACT

The transreflectors may comprise a transparent substrate having reflective surfaces and other light transmissive surfaces for respectively reflecting and transmitting a greater portion of the light striking opposite sides of the substrate. Alternatively, the transreflectors may comprise two or more transparent substrates of different indices of refraction bonded together, with a pattern of optical deformities in the mating side of one of the substrates and an inverse pattern of optical deformities in the mating side of an other substrate in mating engagement with each other. The transreflectors are used in a transreflector system or display to transmit more of the light emitted by a backlight or other light source incident on one side of the transreflectors and reflect more of the light incident on the opposite side of the transreflectors. The transreflectors and backlight may be tuned to each other to enable the transreflectors to better transmit more of the light emitted by the backlight.

59 Claims, 15 Drawing Sheets

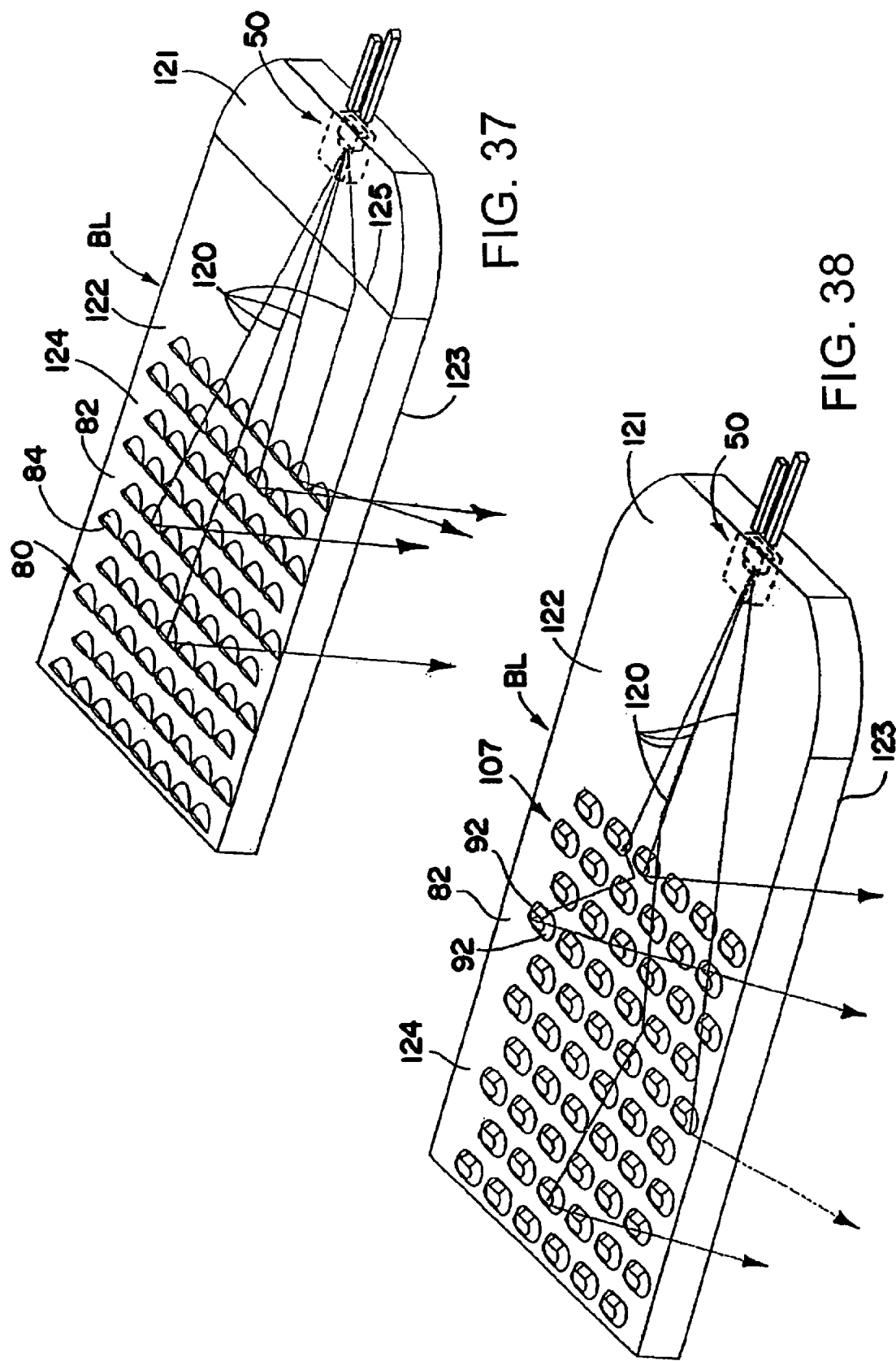

TRANSREFLECTORS, TRANSREFLECTOR SYSTEMS AND DISPLAYS AND METHODS OF MAKING TRANSREFLECTORS

CROSS-REFERENCE TO RELATED APPLICATIONS

This application is a continuation-in-part of U.S. patent application Ser. No. 09/256,275, filed Feb. 23, 1999 now U.S. Pat. No. 6,712,481, the entire disclosure of which is incorporated herein by reference.

FIELD OF THE INVENTION

This invention relates to transreflectors that reflect a greater portion of the light that strikes one side of the transreflectors and transmit a greater portion of the light that strikes the other side of the transreflectors or vice versa. Also, this invention relates to different methods of making transreflectors.

BACKGROUND OF THE INVENTION

A transreflector is an optical device that transmits part of the light that strikes it and reflects part of the light that strikes it. An example of a transreflector is a beam splitter or half-silvered mirror. Consider the light intensity that strikes a given side of a transreflector, by conservation of energy, the sum of the light intensity that is (i) transmitted through the transreflector, (ii) reflected by the transreflector and (iii) absorbed by the transreflector must equal the original intensity striking that side. If one desires to construct a transreflector that transmits as much of the light striking one side of the device as possible while also reflecting as much of the light striking the opposite side of the device as possible, a beam splitter type transreflector device is theoretically limited to 50% light transmission and 50% light reflection assuming that the intensity of the light absorbed by the device is zero. Since it is not physically possible to create a transreflective device that has zero light absorption, a beam splitter type transreflector device that attempts to both transmit and reflect the maximum amount of light incident on the device will be limited to less than 50% transmission and less than 50% reflection.

Transreflectors may be used, for example, with liquid crystal displays (LCDs), used in laptop computers, personal digital assistant devices (PDA), word processors, avionic displays, cell phones and the like to permit the displays to be illuminated in dark environments by a backlight and in lighted environments by ambient light without the need to power the backlight. This is done, for example, by placing the transreflector between the backlight and the LCD. In lighted environments a portion of the ambient light passes through the display and a portion of this light is then reflected by the transreflector back through the LCD to illuminate the display. In dark environments, a portion of the light from the backlight is transmitted through the transreflector and through the LCD to illuminate the display.

In order to make the display as bright as possible in both lighted and dark environments, the ideal transreflector would transmit 100% of the light from the backlight striking it from below and reflect 100% of the ambient light striking it from above. Optical losses in the transreflective device, absorption for example, make it impossible to obtain 100% transmittance of light striking the transreflector from below and 100% reflection of light striking the transreflector from above. However, it is desirable to be as close to 100% transmittance and 100% reflection as practically possible.

Beam splitter type transreflectors treat light striking the top surface from above and light striking the bottom surface from below the same, and are limited to less than 50% for both transmission and reflection of light striking a surface of these devices. Therefore, beam splitter type transreflective devices are limited to transmitting less than 50% of the light from the backlight striking them from below and reflecting less than 50% of the ambient light striking them from above, which falls far short of the ideal 100% transmission from below and 100% reflectance from above needed to make a display as bright as possible.

In order to make displays as bright as possible, there is a need for transreflective devices which treat light striking them from above differently than light striking them from below. In addition these transreflectors should transmit as much of the light that strikes them from below as possible (e.g., greater than 50%), and reflect as much of the light that strikes them from above as possible (e.g., greater than 50%).

SUMMARY OF THE INVENTION

The present invention relates to transreflectors, transreflector systems and displays and methods of making transreflectors that reflect more of the light that strikes one side of the transreflectors and transmit more of the light that strikes the opposite side of the transreflectors.

In one form of the invention, the transreflector comprises a transparent substrate (which may be a film or plate) having a pattern of optical deformities possessing reflective and non-reflective light transmissive surfaces on or in one side of the substrate. The term "transparent" as used throughout the specification and claims means optically transparent or optically translucent. The transreflector may also comprise two or more substrate/film layers that have been bonded together with the optical deformities on outer surfaces of the outermost layers. These optical deformities may comprise grooves or individual optical deformities of well defined shape. Also, the size, height, shape, position, angle, density, and/or orientation of the optical deformities may vary across the substrate. The reflective surfaces are coated with a reflective coating that may comprise a polarization coating. The transmissive surfaces may be textured, lensed or have optical shapes to redirect light, and may also have an optical coating such as an antireflective or polarization coating. The pattern of reflective and non-reflective light transmissive surfaces may be on the top side of the substrate (i.e., the surface nearest the LCD) or the bottom side of the substrate (i.e., the surface nearest the backlight). The reflective and transmissive surfaces may vary in size, shape, angle, density and orientation.

In the case where the pattern of reflective and non-reflective surfaces are on the top side of the transreflector, the other side or bottom of the transreflector may either be planar or have optical shapes designed to better transmit a certain distribution of light, for example the output distribution of a backlight, and may in addition direct this light to the light transmissive surfaces. These optical deformities may comprise grooves or individual optical deformities of well defined shape. Also, the size, height, shape, position, angle, density, and/or orientation of the optical deformities may vary across the transreflector. An optical coating such as an antireflective or polarization coating may also be applied to the bottom of the transreflector in addition to or in place of the optical deformities.

In the case where the pattern of reflective and non-reflective surfaces are on the bottom side of the transreflector, the other side or top of the transreflector may either be planar or have optical deformities to redirect light. For example, the top side of the transreflector may have optical shapes which redirect light transmitted through the transreflector more toward the normal direction of the LCD so that more light from the transreflector is transmitted through the LCD. These optical deformities may comprise grooves including but not limited to prismatic or lenticular grooves, or individual optical deformities of well defined shape. Also, the size, shape, angle, density, and orientation of the optical deformities may vary across the transreflector. The top surface of the transreflector may also be textured or have an optical coating such as an antireflective or polarization coating.

Such a transreflector may be made by applying a reflective coating to one side of a transparent substrate and then thermoforming such one side to provide a plurality of spaced angled reflective coated surfaces and a plurality of angled non-coated light transmissive surfaces. The angles of both the reflective and non-reflective light transmissive surfaces may be chosen to optimize performance. Also, optical deformities may be formed on the other side of the substrate.

Alternatively, such a transreflector may be made by thermoforming one side of a transparent substrate to produce a plurality of spaced angled surfaces and a plurality of other angled surfaces, and then applying a reflective coating on the angled surfaces to make them reflective surfaces while leaving the other angled surfaces uncoated. This can be accomplished, for example, by depositing a reflective coating onto the angled surfaces but not onto the other angled surfaces using a line of site or other appropriate deposition technique.

In another form of the invention, the transreflector comprises two or more transparent substrates of different indices of refraction bonded together along mating sides of the substrates. The mating side of at least one of the substrates has a pattern of optical deformities and the mating side of the other substrate has an inverse pattern of the optical deformities on the mating side of the one substrate. The other side of the substrate that has the lower index of refraction may be planar or have optical deformities designed to accept a specific distribution of light emitted from a backlight or other light source. The other side of the substrate with the higher index of refraction may be textured or have optical shapes to redirect light entering or exiting the transreflector from this surface. The other side of either substrate may also have an optical coating applied such as an antireflective or polarization coating. An optical coating may also be applied to either of the mating surfaces before the two substrates are bonded together, resulting in an optical film at the mating interface of the two substrates after the two substrates are bonded together.

Such a transreflector may be made by preforming a pattern of optical deformities on or in one side of the two transparent substrates of different indices of refraction and using the preformed pattern of optical deformities of the one substrate to form an inverse pattern of the optical deformities in or on one side of the other substrate by melting or heat softening one side of the other substrate and pressing the melted or softened side of the other substrate against the preformed pattern of deformities on or in one side of the one substrate to form the inverse pattern on or in the one side of the other substrate while preventing such one side of the one substrate from melting. Both of the substrates are then cooled to cause the one side of the other substrate to solidify and bond with the one side of the one substrate. Also, optical deformities may be formed on or in the other side of either of the substrates either before, after or during bonding of the two substrates together.

Any of these transreflectors may be used in a transreflector system or display to transmit light emitted by a backlight or other light source incident on one side of the transreflectors and for reflecting ambient light incident on the opposite side of the transreflectors. The side of the transreflectors that receives incident light from a backlight or other light source may have optical deformities designed to better transmit a particular output distribution of the light emitted from the light source, and may include an angular shape pattern that changes with the distance from the input edge of a backlight to compensate for changes in the angular distribution of the light emitted from the backlight as the distance from the input edge of the backlight increases. The optical deformities on the side of the transreflectors that receive light from the backlight or other light source may comprise grooves or individual optical deformities of well defined shape. Also, the size, shape, angle, density, and orientation of the optical deformities may vary across the transreflectors.

The other side of the transreflectors which receives incident ambient light may be textured or have optical shapes to redirect light entering or exiting the transreflectors from this surface. The optical shapes on the side of the transreflectors that receive ambient light may comprise grooves or individual optical deformities of well defined shape. Also, the size, shape, angle, density, and orientation of the optical deformities may vary across the transreflectors. An optical coating such as an antireflective or polarization coating may also be applied to either surface of the transreflectors in addition to or in place of the optical deformities.

Likewise, the backlight may have a pattern of individual optical deformities for producing a particular light output distribution from its light emitting surface that have a well defined shape including at least one sloping surface for reflecting or refracting light impinging on the optical deformities out of the light emitting surface. The sloping surface of at least some of these deformities may be oriented to face an optically coupled area of the light input edge across the backlight. Also, at least some of the deformities, which may comprise depressions in or projections on the light emitting portion of the backlight/panel member, may vary in size, shape, depth or height, density and/or orientation across the backlight. Moreover, the deformities may be randomized, staggered, or arranged in a stochastic pattern across the backlight. Further, at least some of the deformities may be arranged in clusters across the backlight, with at least some of the deformities in each of the clusters having a different size or shape characteristic that collectively produce an average size or shape characteristic for each of the clusters that varies across the backlight. This allows the light output distribution of the backlight and the light input surfaces on the transreflectors that receive incident light from the backlight to be tuned to each other so that the transreflectors will better transmit more of the light emitted by the backlight. Also the side of the backlight closest to the transreflector may have optical deformities which align with the deformities on or in the transreflector to increase the efficiency with which light is transmitted from the backlight to the transreflector. The region between the aligned backlight and transreflector deformities may contain a refraction index matching material to further increase efficiency. A display may be placed in close proximity to the side of the transreflectors facing away from the backlight.

To the accomplishment of the foregoing and related ends, the invention, then, comprises the features hereinafter more fully described and particularly pointed out in the claims, the following description and annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIGS. 37 and 38 are enlarged perspective views schematically showing how exemplary light rays emitted from a focused light source are reflected or refracted by different individual optical deformities of well defined shapes of a backlight surface area in accordance with this invention.

DETAILED DESCRIPTION OF THE INVENTION

Figure 1:
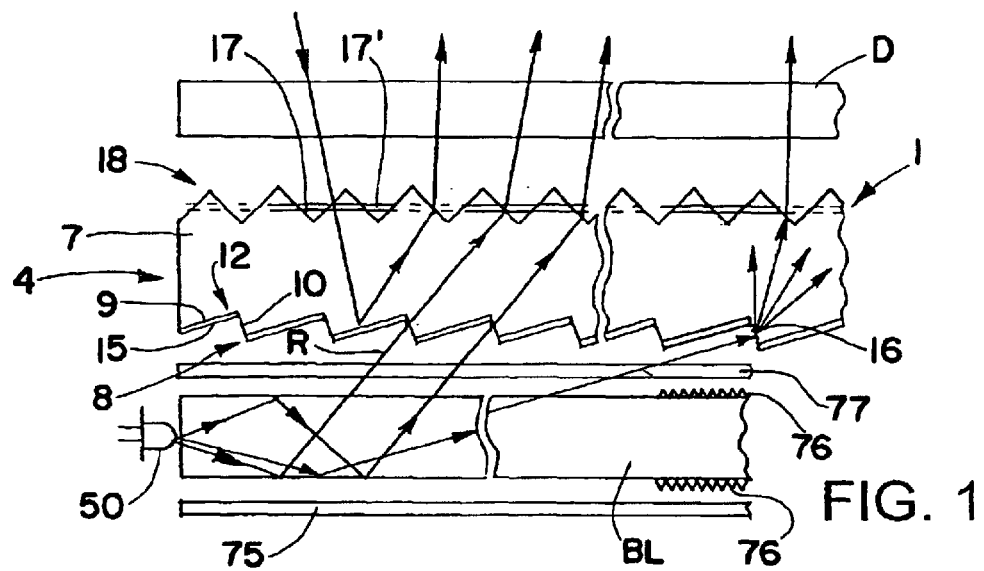
FIG. 1 is a schematic side elevation view of one form of transreflector system in accordance with the present invention.
Figure 2:
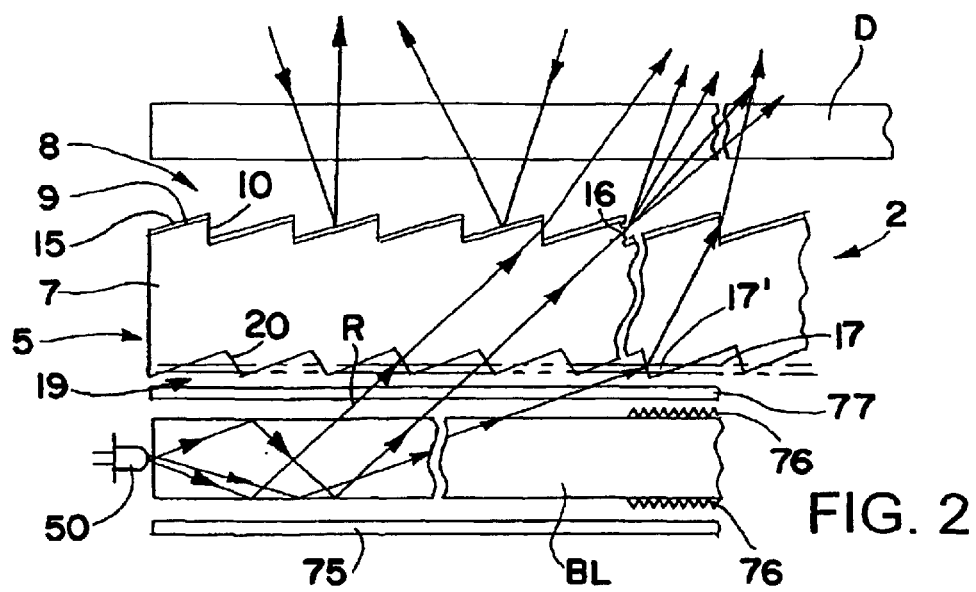
FIGS. 2 and 3 are schematic side elevation views of other forms of transreflector systems in accordance with the present invention.
Figure 3:
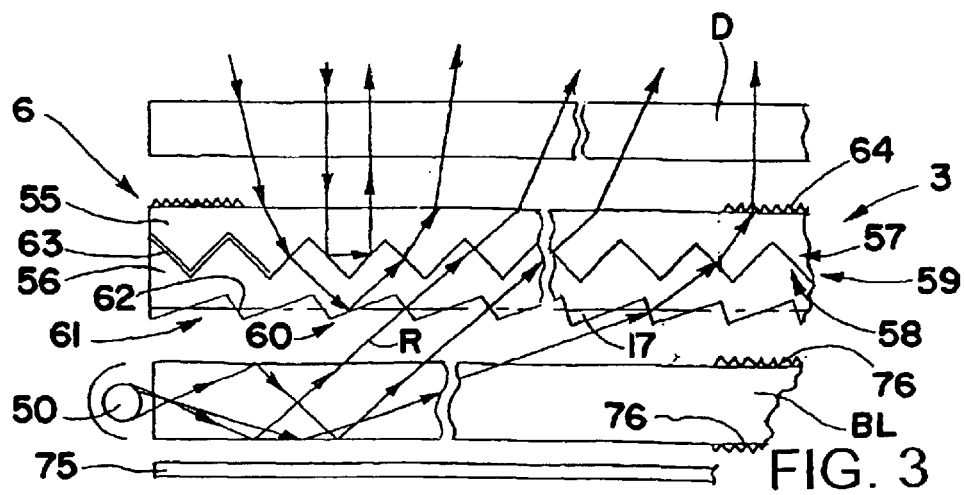

Referring now in detail to the drawings, and initially to FIGS. 1–3, these figures schematically show three different transreflector systems 1, 2 and 3 in accordance with this invention each including a transreflector 4, 5 and 6 placed between a display D such as a liquid crystal display or membrane switch and a backlight BL for reflecting more of the ambient light that passes through the display back out the display making it more visible (e.g., brighter) in a lighted environment, and for transmitting more of the light from the backlight through the transreflector and out the display to illuminate the display in a dark environment.

Figure 4A:
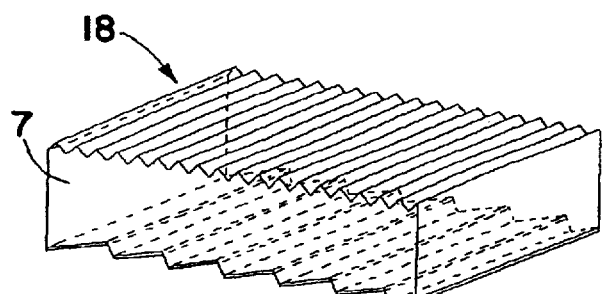
FIGS. 4a–4c are schematic perspective views of a transreflector of the type shown in FIG. 1 in which the optical deformities on one side of the transreflector are comprised of grooves.
Figure 4B:
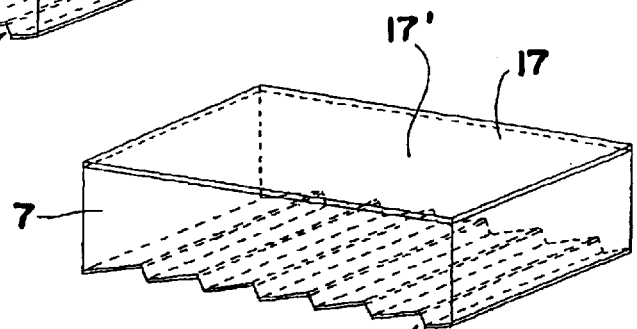
Figure 4C:
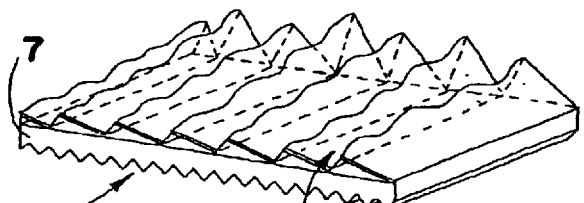
Figure 5A:
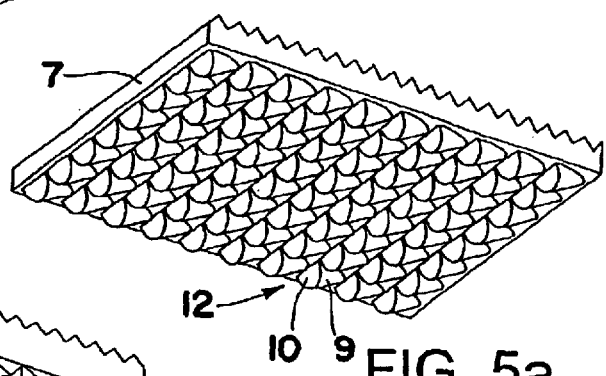
FIGS. 5a–5d are schematic perspective views of a transreflector of the type shown in FIG. 1 in which the optical deformities on one side of the transreflector are individual optical deformities each having a well defined shape.
Figure 5B:
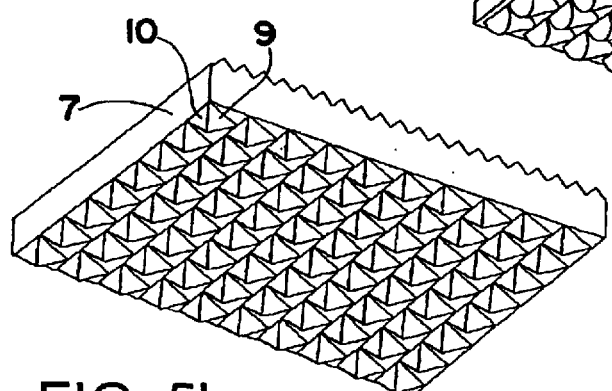
Figure 5C:
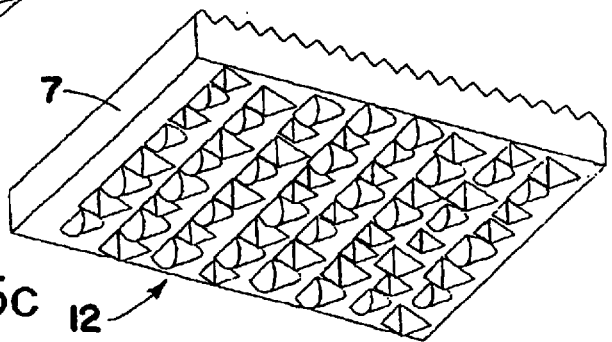

Each of the transreflectors 4, 5 shown in FIGS. 1 and 2 comprises a transparent (i.e., optically transparent or translucent) substrate 7 which may be a plate or film including a multilayer film comprising for example a carrier film and an ultra-violet curable layer. On or in one side of the substrate are a plurality of spaced optical elements or deformities 8 each including one or more light reflective surfaces 9 and a non-reflective light transmissive surface 10. The deformities 8 may either be grooves 11 as schematically shown in FIGS. 4a–c or a pattern of individual optical deformities 12 each having a well defined shape as schematically shown in FIGS. 5a–d. The grooves 11 may be of the same height throughout their length as schematically shown in FIGS. 4a and 4b or may vary in height along their length as schematically shown in FIG. 4c. Also the variation in height may be different from one groove 11 to another as further schematically shown in FIG. 4c. Each of the individual optical deformities 12 may be of substantially the same size and shape as schematically shown in FIGS. 5a and 5b or of different sizes and geometric shapes as schematically shown in FIG. 5c. The optical deformities 12 shown in FIG. 5a each have only two surfaces, a planar reflective surface 9 and a curved light transmissive surface 10, whereas the optical deformities 12 shown in FIG. 5b each have a pyramidal shape including a plurality of reflective surfaces 9 and one light transmissive surface 10.

Figure 1A:
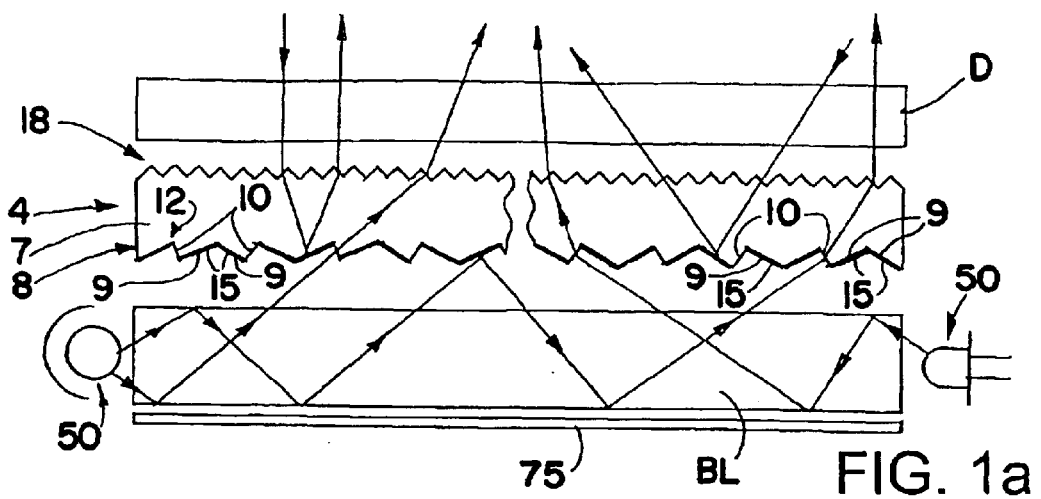
FIGS. 1a–1c are schematic side elevation views of different variations of the transreflector system shown in FIG. 1.
Figure 5D:
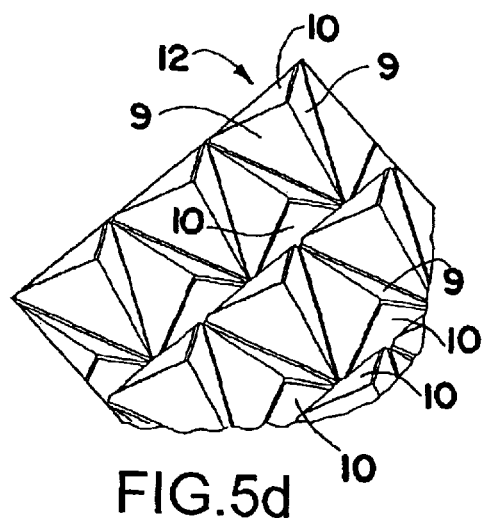

Also each of the optical deformities 12 may be arranged in a pattern with the light transmissive surface 10 of each of the deformities facing the same general direction as schematically shown in FIGS. 1 and 5a–5c for receiving light from a backlight lit by a single light source 50 optically coupled to one input edge only as schematically shown in FIG. 1 or arranged in a pattern with the light transmissive surfaces 10 and light reflective surfaces 9 of different optical deformities 12 generally facing in opposite directions as schematically shown in FIGS. 1a and 5d for receiving light from a backlight lit by two light sources 50 optically coupled to two input edges as schematically shown in FIG. 1a.

Figure 6A:
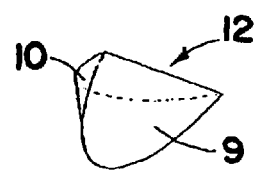
FIGS. 6a–6e are schematic perspective views of other geometric shapes that the individual optical deformities of FIGS. 5a–5d may take.
Figure 6B:
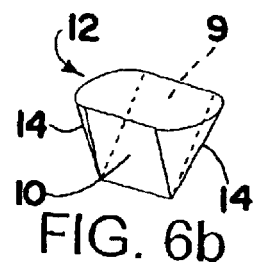
Figure 6C:
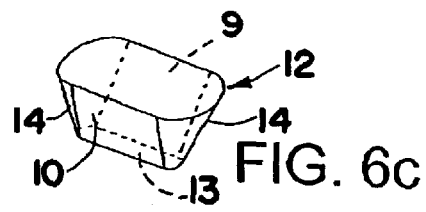
Figure 6D:
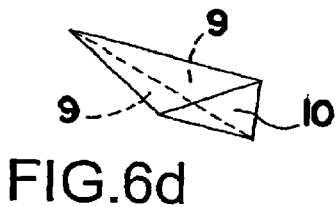
Figure 6E:
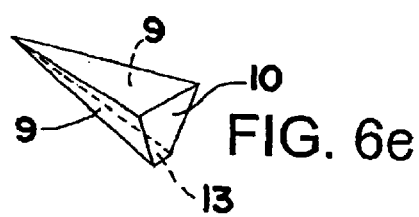

In FIG. 5a the reflective surface 9 of the individual optical deformities 12 is rounded or curved and the light transmissive surface 10 is planar. However, it will be appreciated that the reflective surface 9 of the individual optical deformities 12 may be planar and the light transmissive surface 10 rounded as schematically shown in FIG. 6a. Alternatively, both the reflective surface(s) 9 and light transmissive surface 10 of the individual optical deformities 12 may be planar as schematically shown in FIGS. 6b–6e. Also, the reflective surface(s) 9 and light transmissive surface 10 of the individual optical deformities 12 may intersect each other as schematically shown in FIGS. 5a–5d and 6a, 6b and 6d or may be spaced from each other by an intermediate surface 13 extending parallel to the general plane of the transreflectors as schematically shown in FIG. 6c or intersecting the general plane of the transreflectors as schematically shown in FIG. 6e. Moreover, the individual optical deformities may have rounded or curved ends 14 as schematically shown in FIGS. 6b and 6c.

The light transmissive surfaces 10 are angled to transmit a greater portion of the light from the backlight and direct the light through the transreflector and out through the other side of the transreflector. Also the projected area of the light transmissive surfaces 10 onto a plane normal to the maximum output angle of the light rays R emitted from the backlight BL is substantially less than the projected area of the reflective surfaces 9 onto the general plane of the transreflectors 4, 5. This enables the reflective surfaces 9 to reflect more of the ambient light passing through the display D back through the display as schematically shown in FIGS. 1 and 2 making the display more visible (e.g., brighter) in a lighted environment. At the same time, the light transmissive surfaces 10 will transmit more of the light incident on the transreflectors 4, 5 from a backlight BL or other light source out the display to illuminate the display in a dark environment.

The reflective surfaces 9 are coated with a suitable reflective coating 15 such as a metallized coating which may also comprise a polarization coating, whereas the light transmissive surfaces 10 may be textured or lensed as schematically shown for example at 16 in FIGS. 1 and 2 to redirect the light passing through the light transmissive surfaces.

In the embodiment shown in FIG. 1, the side of the transreflector 4 furthest from the display D includes the reflective surfaces 9 and associated light transmissive surfaces 10, whereas in the embodiment shown in FIG. 2, the side of the transreflector 5 closest to the display D includes the reflective surfaces 9 and associated light transmissive surfaces 10. In either case, a greater portion of the ambient light that passes through the display will be reflected by the reflective surfaces 9 back through the display making it more visible in a lighted environment.

Figure 1B:
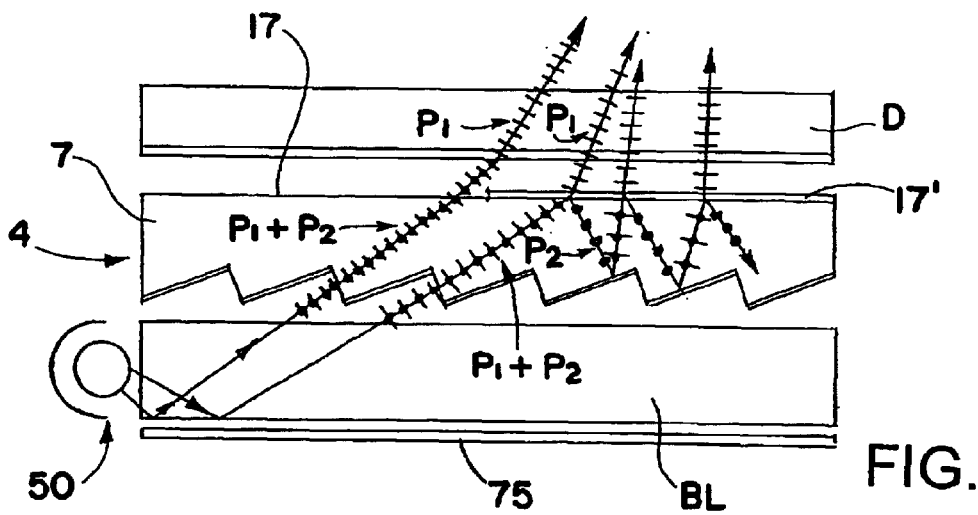

In a dark environment, in the case of the transreflector 4 shown in FIG. 1, the light transmissive surfaces 10 between the reflective surfaces 9 on the side of the transreflector closest to the backlight BL are angled to transmit a greater portion of the light from the backlight and direct the light through the transreflector and out through the other side of the transreflector. The other side of the transreflector 4 may be planar as shown in phantom lines 17 in FIG. 1 and in solid lines in FIGS. 1b and 4b, or have a texture, chemical etch or laser etch or have optical deformities 18 in or on the other side of the transreflector as shown in solid lines in FIGS. 1, 1a, 1c, 4a and 4c to redirect the light more toward the normal direction of the display D to better illuminate the display in a dark environment. The other side may also have an optical film (coating, layer) such as an antireflection or polarization recycling film 17' (shown in phantom lines in FIG. 1 and in solid lines in FIG. 4b and only on the right hand side of FIG. 1b for purposes of comparison). The light that is emitted from the backlight BL is unpolarized (i.e., made up of two polarizations $P_1$ and $P_2$ as schematically shown in FIG. 1b. When this unpolarized light hits the polarization recycling coating 17', polarization $P_1$ is transmitted and polarization $P_2$ is reflected. Polarization $P_1$ continues and is transmitted through the LCD. Polarization $P_2$ is reflected back into the transreflector where it reflects and is scattered back toward the reflective polarizer 17', once again becoming a mixture of both polarizations $P_1$ and $P_2$ and the process repeats.

If the reflective polarization film 17' is not present as shown for comparison of function on the left hand side of the transreflector in FIG. 1b, the unpolarized light $P_1$ and $P_2$ that leaves the backlight BL and is transmitted by the transreflector strikes the LCD and polarization $P_1$ is transmitted by the LCD while polarization $P_2$ is absorbed resulting in a loss of substantially 50% of the light.

In the case of the transreflector 5 shown in FIG. 2, the other side of the transreflector may either be planar as shown by phantom lines 17 in FIG. 2, or have a texture, chemical etch or laser etch or optical deformities 19 as shown in solid lines in FIG. 2 including surfaces 20 angled to transmit light from the backlight or other light source and direct the light to the light transmissive surfaces 10 in the side of the transreflector closest to the display D for increasing the amount of light transmitted from the backlight through the transreflector to illuminate the display. The other side may also have an optical coating 17' such as an antireflection or polarization coating. These optical deformities 18, 19 can either be grooves or individual deformities each having a well defined shape as described hereafter.

Figure 7A:
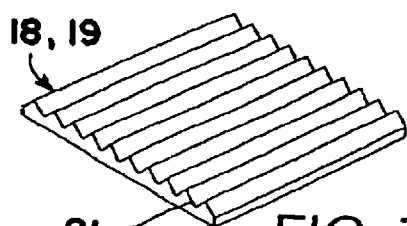
FIGS. 7a–7g are schematic perspective views of different patterns of optical deformities on or in one or more other surfaces of the transreflectors of FIGS. 1–3.
Figure 7B:
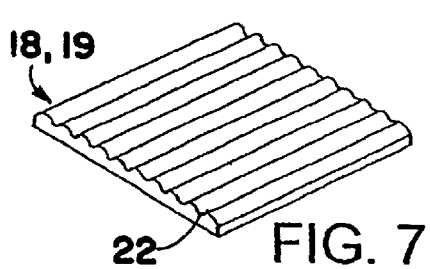
Figure 7C:
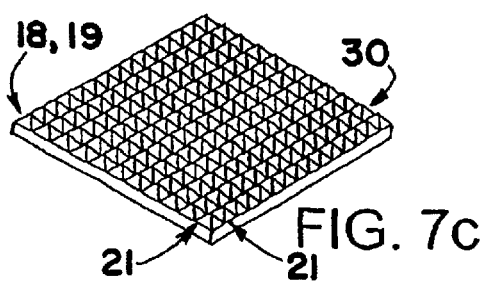
Figure 7D:
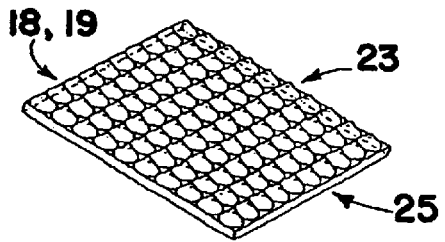
Figure 7E:
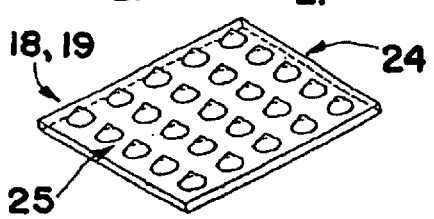
Figure 7F:
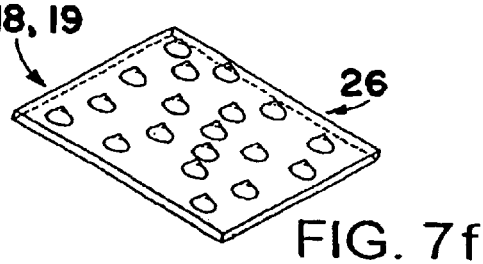
Figure 7G:
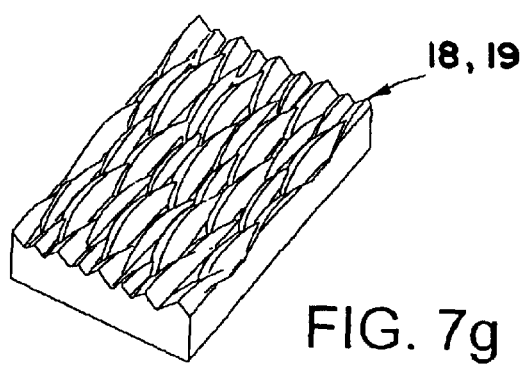

The optical deformities 18 in or on the top side of the transreflector 4 shown in FIG. 1 and the optical deformities 19 in or on the bottom side of the transreflector 5 shown in FIG. 2 may consist of prismatic or lenticular grooves 21, 22 of the type schematically shown, for example, in FIGS. 7a and b or two sets of grooves 21 or 22 cut perpendicular to each other (e.g., cross grooves) resulting in a pyramid structure 30 as schematically shown in FIG. 7c. Alternatively, such optical deformities 18, 19 may consist of a pattern of individual optical deformities each having a well defined shape that may be in a close array 23 as shown in FIG. 7d or in a spaced array 24 as shown in FIG. 7e, and may either be in rows 25 as shown in FIGS. 7d and e or randomized as shown at 26 in FIG. 7f. Moreover, the pattern of individual optical deformities 18, 19 may randomly overlap each other with the optical deformities either being staggered with respect to each other or intersecting or interlocking each other as schematically shown in FIG. 7g. Also, the position, size, height, density, angle, orientation and/or shape of the optical deformities may vary across the substrate.

Figure 8A:
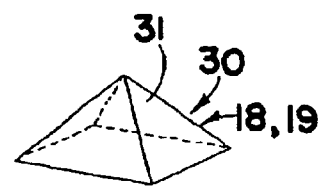
FIGS. 8a–8i are schematic perspective views of different geometric shapes of individual optical deformities that can be substituted for the optical deformities shown in FIGS. 7c–e.
Figure 8B:
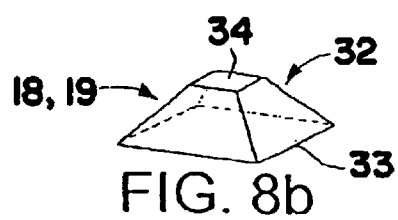
Figure 8C:
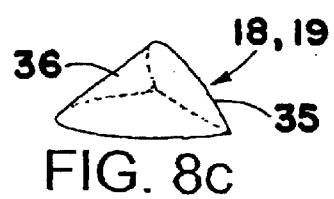
Figure 8D:
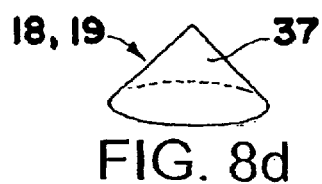
Figure 8E:
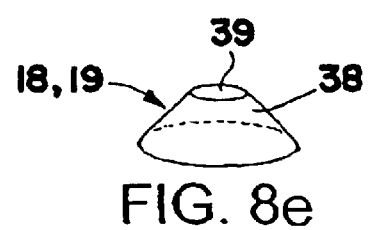
Figure 8F:
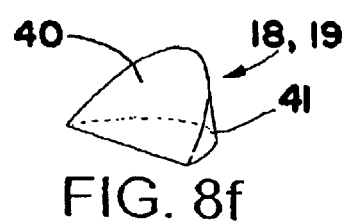
Figure 8G:
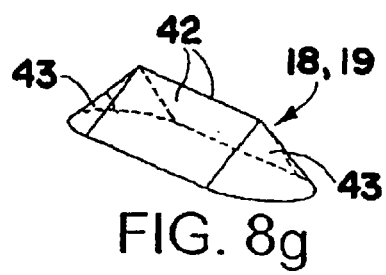
Figure 8H:
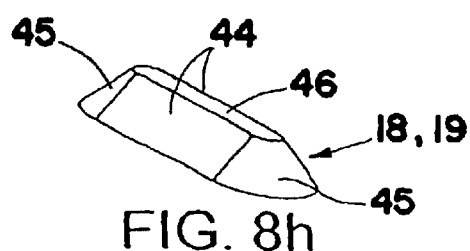
Figure 8I:
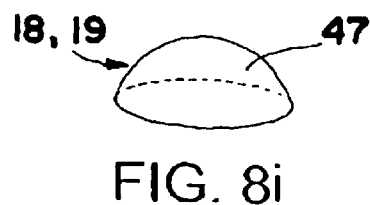

The individual optical deformities 18, 19 may also take many different shapes including, for example, a pyramid 30 with triangular shape sides 31 as shown in FIG. 8a, a frusto-pyramid 32 with trapezoidal shape sides 33 and a planar top 34 as shown in FIG. 8b, a relatively steep planar angled surface 35 with long rounded or curved sides 36 as shown in FIG. 8c, a conical shape 37 as shown in FIG. 8d, a frusto-conical shape 38 with a planar top 39 as shown in FIG. 8e, a relatively shallow sloping planar surface 40 with steeper rounded or curved sides 41 as shown in FIG. 8f, a pair of intersecting oppositely sloping sides 42 with oppositely rounded or curved ends 43 as shown in FIG. 8g, a pair of oppositely sloping planar sides 44 with oppositely rounded or curved ends 45 and a planar top 46 as shown in FIG. 8h, and a semispherical shape 47 as shown in FIG. 8i. Moreover, more than one type of shape of optical deformities 18, 19 may be provided in or on one or both sides of the transreflector.

In any case, the patterns of the position, angle, density, size, height, shape and orientation of the deformities on the side of the transreflectors 4, 5 closest to the backlight are designed to transmit a specific light distribution from the backlight. To that end, the angles of the surfaces 10 of transreflector 4 and surfaces 20 of transreflector 5 may be varied as the distance from the light source 50 increases to account for the way the backlight BL emits light differently as the distance from the light source increases.

Figure 9A:
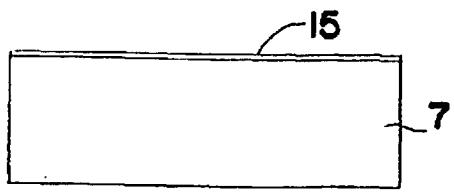
FIGS. 9a–9c are schematic illustrations of one method of making the light reflective and transmissive surfaces of the transreflectors shown in FIGS. 1 and 2.
Figure 10A:
FIGS. 10a–10c are schematic illustrations of another method of making the light reflective and transmissive surfaces of the transreflectors shown in FIGS. 1 and 2.
Figure 9B:
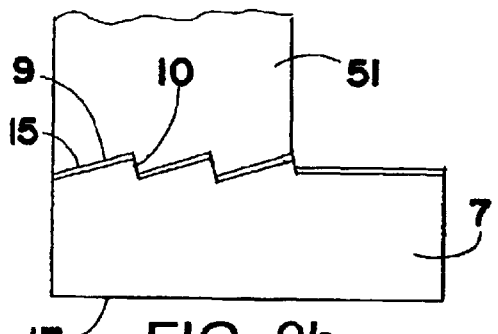
Figure 9C:
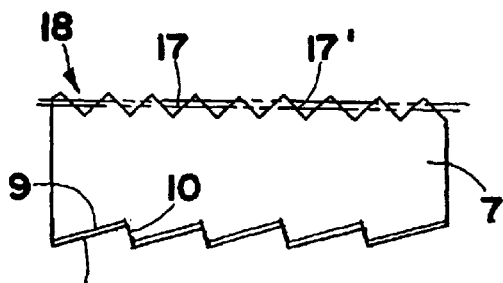

FIGS. 9 and 10 show two different methods of making the light reflective and light transmissive surfaces 9 and 10 of the transreflectors 4 and 5 shown in FIGS. 1 and 2. In the method shown in FIG. 9, a reflective film, layer or coating 15 may be applied to one side of a transparent substrate 7 which may be comprised of one or more layers each having a constant index of refraction (see FIG. 9a). Then the reflective coating may be removed from selected surfaces or areas as by thermoforming the coated side of the transparent substrate using a press or roller 51 to form a plurality of spaced angled or sloping reflective coated surfaces or areas 9 separated by a plurality of spaced other angled or sloping noncoated light transmissive surfaces or areas 10 as shown in FIGS. 9b and 9c. During or after the thermoforming process, the light transmissive surfaces 10 may be textured or lensed for redirecting light passing through the light transmissive surfaces as desired. The other side of the substrate 7 may be left planar as shown in solid lines 17 in FIG. 9b and phantom lines 17 in FIG. 9c or textured or provided with optical deformities 18 as shown in solid lines in FIG. 9c. Also an optical coating 17' may be applied to the other side as further shown in phantom lines in FIG. 9c.

Figure 10B:
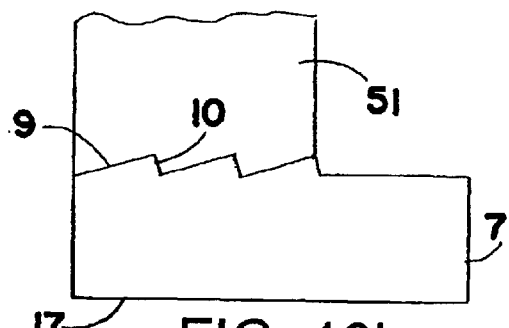
Figure 10C:
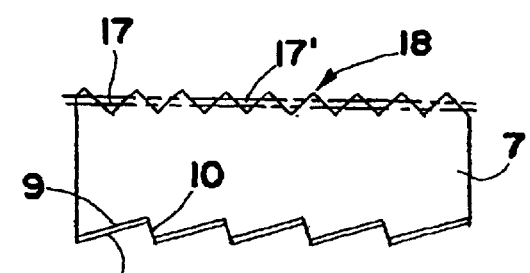

The method shown in FIG. 10 differs from that shown in FIG. 9 in that no reflective coating is applied to the transparent substrate 7 until after one side of the substrate is thermoformed to produce a plurality of spaced angled or sloping surfaces 9 separated by a plurality of other angled or sloping surfaces 10 as shown in FIG. 10b. Then a reflective coating 15 is applied only on the angled surfaces 9 as shown in FIG. 10c using for example a line of site deposition technique to form the reflective surfaces 9 while leaving the light transmissive surfaces 10 uncoated. Alternatively, the reflective coating 15 may be hot stamped onto the reflective surfaces 9.

Figure 3A:
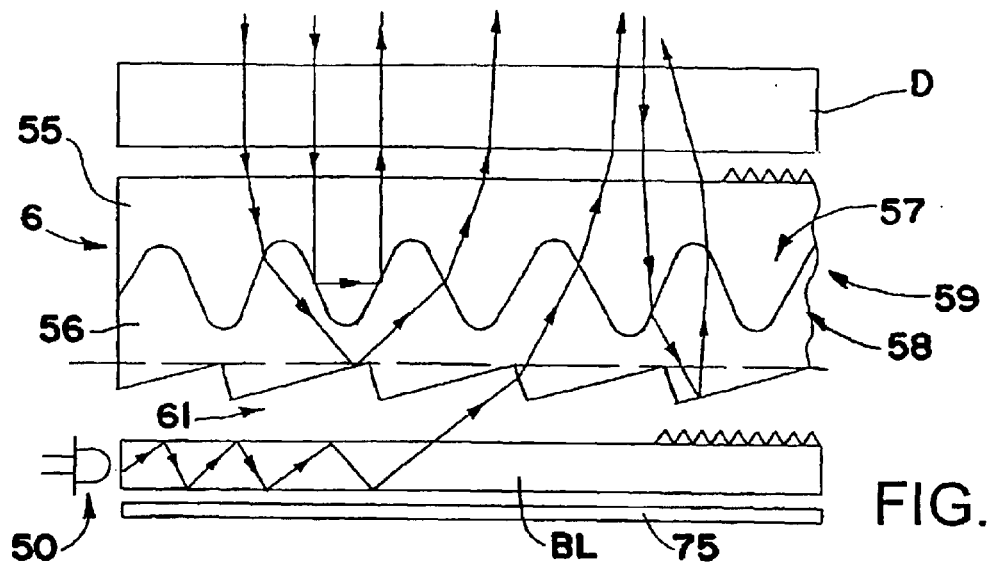
FIGS. 3a–3c are schematic side elevation views of different variations of the transreflector system shown in FIG. 3.
Figure 3B:
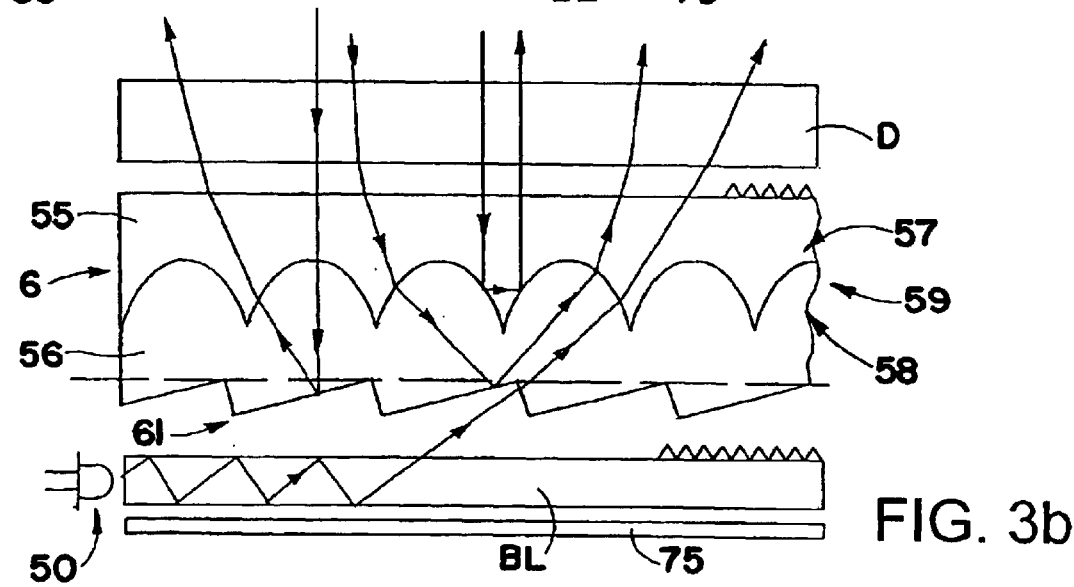

The transreflector 6 shown in FIG. 3 differs from those shown in FIGS. 1 and 2 in that it comprises at least two transparent substrates 55, 56 of different indices of refraction bonded together, with optical deformities 57, 58 at the interface 59 between the two substrates. The substrates 55, 56 may be completely or partially bonded together or bonded together in selected areas as desired. The substrate 55 closest to the display D has a higher index of refraction than the substrate 56 furthest from the display. The mating side of one of the substrates (for example substrate 55) includes a pattern of optical deformities 57 and the mating side of the other substrate 56 includes an inverse pattern of optical deformities 58. These optical deformities may comprise grooves of different shapes including for example prismatic grooves having planar sides with sharp or curved peaks and valleys as shown in FIGS. 3 and 3a, respectively, or curved sides as shown in FIG. 3b or lenticular grooves or cross grooves or individual optical deformities each having a well defined shape as previously described and schematically illustrated in FIGS. 7 and 8 such that the difference in the indices of refraction of the two substrates causes a greater portion of the ambient light that passes through the display and enters the higher index side 55 of the transreflector 6 to be totally internally reflected at both the interior high/low interface 59 between the two substrates and at the bottom low/air interface 60 to make the display more visible in a lighted environment.

Light rays R from the backlight BL enter through the lower index side 56 of the transreflector 6 and are transmitted through the transreflector to the display D. The side 17 of the lower index substrate 56 closest to the backlight BL may be either planar as shown in phantom lines in FIG. 3, textured or have a pattern of optical deformities 61 as shown in solid lines in FIG. 3 which may be similar to the optical deformities 19 of the transreflector 5 shown in FIG. 2 to optimize the ability of the transreflector 6 to transmit the specific distribution of light that is emitted from the backlight BL by designing the angle, density, size, shape and orientation of the optical deformities to transmit the specific light distribution emitted from the backlight in the manner previously described. Also, the angles of the light entrance surfaces 62 of the optical deformities 61 of the transreflector 6 may be made to vary as the distance from the light source 50 increases as schematically shown in FIG. 3 to account for the way that the backlight emits light differently as the distance from the light source increases, similar to the light entrance surfaces 10 and 20 of the transreflectors 4 and 5 shown in FIGS. 1 and 2.

Figure 3C:
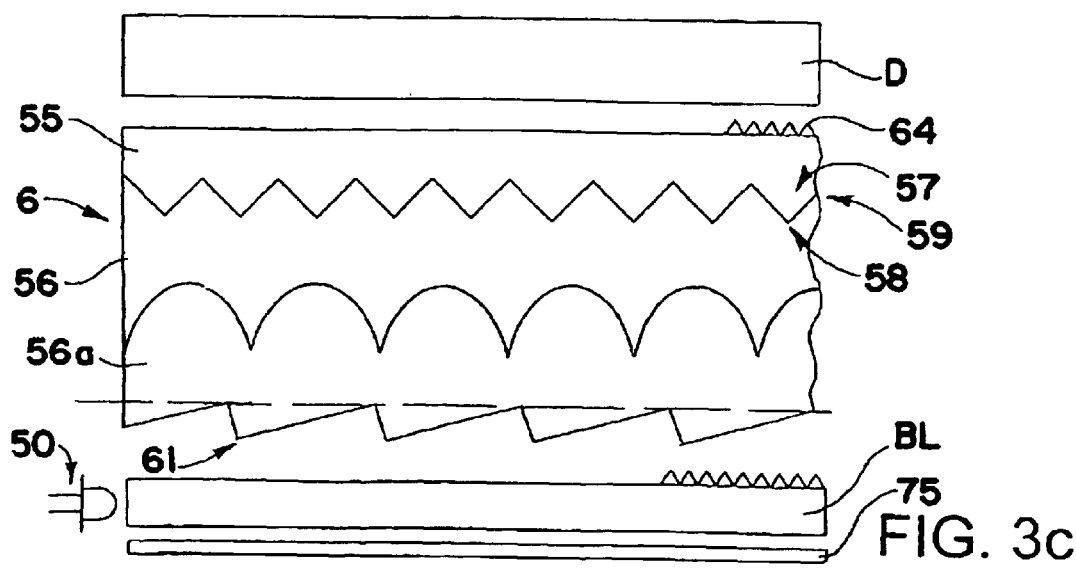

If desired, the interface 59 between the two substrates 55, 56 of the transreflector 6 may be provided with an antireflective, metallized and/or polarization coating 63 as schematically shown in FIG. 3. Also, a diffuser or brightness enhancement film or optical deformities or a texture 64 may be applied to the outer surface of the higher index substrate 55 to obtain a desired light output distribution from the transreflector 6. Further, the transreflector 6 may comprise more than two transparent substrates 55, 56, 56a of different indices of refraction bonded together along mating sides of the substrates with optical deformities on or in the outer surfaces of the outermost layers 55, 56a as schematically shown in FIG. 3c.

Figure 11:
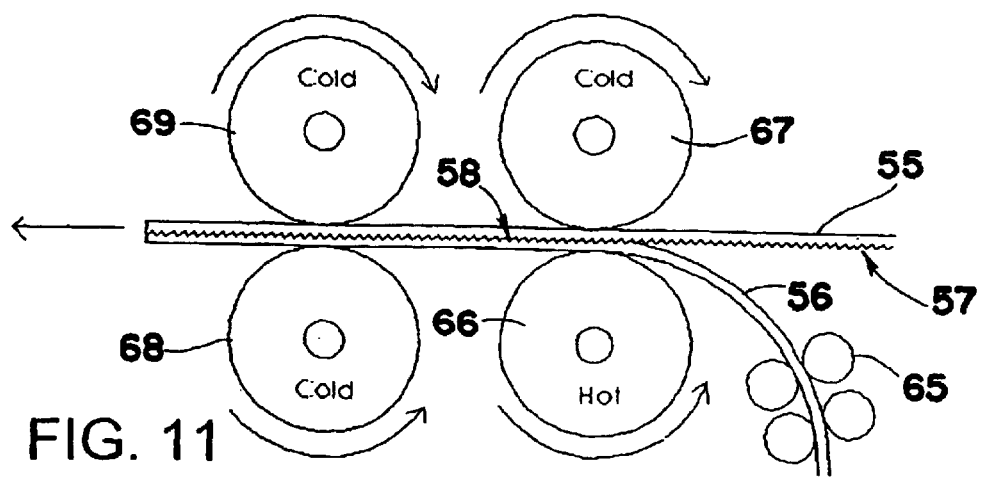
FIG. 11 is a schematic illustration of one method of making the transreflector shown in FIG. 3.

One method of making the transreflector 6 shown in FIG. 3 is to preform the desired pattern of optical deformities 57 in or on one side of one of the substrates (in this case substrate 55) and use the preformed pattern of optical deformities 57 to form an inverse pattern of the optical deformities 58 in or on one side of the other substrate 56 and then bond the two substrates together with the optical deformities 57 and inverse optical deformities 58 in mating engagement with each other as schematically shown in FIG. 11. The inverse pattern of optical deformities 58 may be formed in or on one side of the other substrate 56 by passing the other substrate 56 between a series of preheaters 65 to melt or heat soften the other substrate 56 and then pressing the melted or heat softened substrate 56 against the one substrate 55 using a hot roller 66 which brings the substrate 56 to be formed to its final temperature while preventing the one substrate 55 from melting by passing the one substrate 55 through a cold roller 67 as shown in FIG. 11. Then both substrates 55, 56 may be passed through a pair of cold rollers 68, 69 to cause the melted and/or heat softened substrate 56 to solidify and bond with the preformed substrate 55 as further shown in FIG. 11.

Alternatively, a transparent ultra-violet curable polymer 56 having an index of refraction less than the index of refraction of the substrate 55 may be used in place of the other substrate. The uncured polymer 56 is applied to the preformed pattern of optical deformities 57 in or on one side of the one substrate 55 and then cured to form an inverse pattern of the optical deformities 58 in or on the polymer and bond the polymer to the one side of the one substrate.

The backlight BL may be substantially flat, or curved, or may be a single layer or multi-layers, and may have different thicknesses and shapes as desired. Moreover, the backlight may be flexible or rigid, and be made of a variety of compounds. Further, the backlight may be hollow, filled with liquid, air, or be solid, and may have holes or ridges.

Also, the light source 50 may be of any suitable type including, for example, an arc lamp, an incandescent bulb which may also be colored, filtered or painted, a lens end bulb, a line light, a halogen lamp, a light emitting diode (LED), a chip from an LED, a neon bulb, a cold cathode fluorescent lamp, a fiber optic light pipe transmitting from a remote source, a laser or laser diode, or any other suitable light source. Additionally, the light source 50 may be a multiple colored LED, or a combination of multiple colored radiation sources in order to provide a desired colored or white light output distribution. For example, a plurality of colored lights such as LEDs of different colors (e.g., red, blue, green) or a single LED with multiple color chips may be employed to create white light or any other colored light output distribution by varying the intensities of each individual colored light.

A pattern of optical deformities may be provided on one or both sides of the backlight BL or on one or more selected areas on one or both sides of the backlight as desired. As used herein, the term optical deformities means any change in the shape or geometry of a surface and/or coating or surface treatment that causes a portion of the light to be emitted. These deformities can be produced in a variety of manners, for example, by providing a painted pattern, an etched pattern, machined pattern, a printed pattern, a hot stamp pattern, or a molded pattern or the like on selected areas of the backlight. An ink or print pattern may be applied for example by pad printing, silk printing, inkjet, heat transfer film process or the like. The deformities may also be printed on a sheet or film which is used to apply the deformities to the backlight. This sheet or film may become a permanent part of the backlight for example by attaching or otherwise positioning the sheet or film against one or both sides of the backlight in order to produce a desired effect.

By varying the density, opaqueness or translucence, shape, depth, color, area, index of refraction or type of deformities on or in an area or areas of the backlight, the light output of the backlight can be controlled. The deformities may be used to control the percent of light output from a light emitting area of the backlight. For example, less and/or smaller size deformities may be placed on surface areas where less light output is wanted. Conversely, a greater percentage of and/or larger deformities may be placed on surface areas of the backlight where greater light output is desired.

Varying the percentages and/or size of deformities in different areas of the backlight is necessary in order to provide a substantially uniform light output distribution. For example, the amount of light traveling through the backlight will ordinarily be greater in areas closer to the light source than in other areas further removed from the light source. A pattern of deformities may be used to adjust for the light variances within the backlight, for example, by providing a denser concentration of deformities with increased distance from the light source thereby resulting in a more uniform light output distribution from the backlight.

The deformities may also be used to control the output ray angle distribution from the backlight to suit a particular application. For example, if the backlight is used to backlight a liquid crystal display, the light output will be more efficient if the deformities cause the light rays to emit from the backlight at predetermined ray angles such that they will pass through the liquid crystal display with low loss. Additionally, the pattern of optical deformities may be used to adjust for light output variances attributed to light extractions of the backlight. The pattern of optical deformities may be printed on the backlight surface areas utilizing a wide spectrum of paints, inks, coatings, epoxies or the like, ranging from glossy to opaque or both, and may employ half-tone separation techniques to vary the deformity coverage. Moreover, the pattern of optical deformities may be multiple layers or vary in index of refraction.

Print patterns of optical deformities may vary in shapes such as dots, squares, diamonds, ellipses, stars, random shapes, and the like. Also, print patterns of sixty lines per inch or finer are desirably employed. This makes the deformities or shapes in the print patterns nearly invisible to the human eye in a particular application, thereby eliminating the detection of gradient or banding lines that are common to light extracting patterns utilizing larger elements. Additionally, the deformities may vary in shape and/or size along the length and/or width of the backlight. Also, a random placement pattern of the deformities may be utilized throughout the length and/or width of the backlight. The deformities may have shapes or a pattern with no specific angles to reduce moiré or other interference effects. Examples of methods to create these random patterns are printing a pattern of shapes using stochastic print pattern techniques, frequency modulated half tone patterns, or random dot half tones. Moreover, the deformities may be colored in order to effect color correction in the backlight. The color of the deformities may also vary throughout the backlight, for example, to provide different colors for the same or different light output areas.

In addition to or in lieu of the patterns of optical deformities, other optical deformities including prismatic or lenticular grooves or cross grooves such as shown in FIGS. 7a–c, or depressions or raised surfaces of various shapes using more complex shapes in a mold pattern may be molded, etched, stamped, thermoformed, hot stamped or the like into or on one or more surface areas of the backlight. The prismatic or lenticular surfaces, depressions or raised surfaces will cause a portion of the light rays contacted thereby to be emitted from the backlight. Also, the angles of the prisms, depressions or other surfaces may be varied to direct the light in different directions to produce a desired light output distribution or effect. Moreover, the reflective or refractive surfaces may have shapes or a pattern with no specific angles to reduce moiré or other interference effects.

Figure 1C:
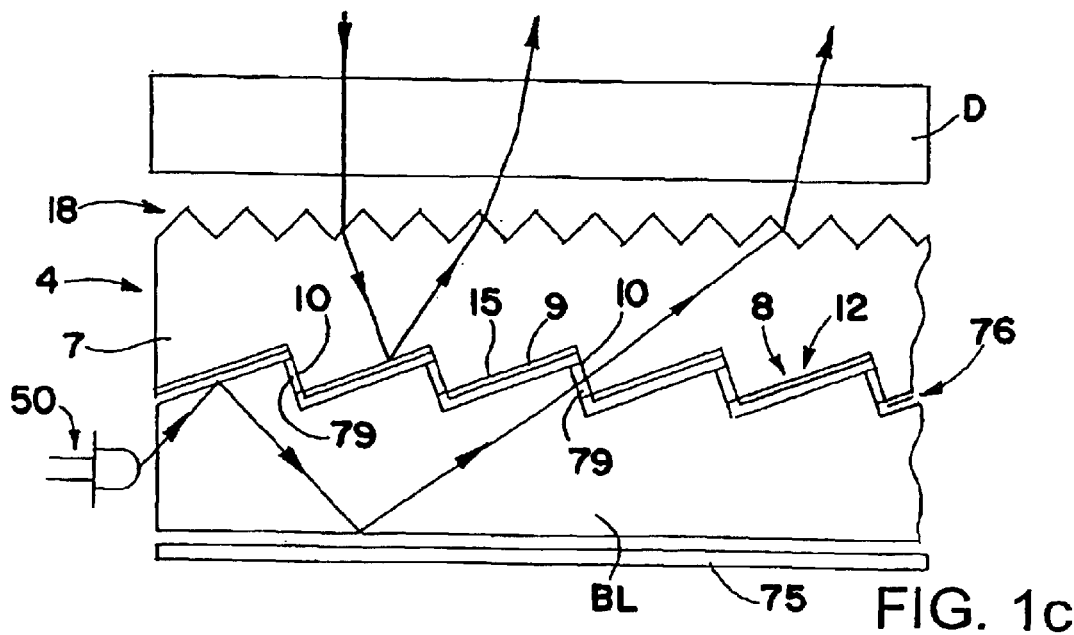

A back reflector 75 may be attached or positioned against one side of the backlight BL as schematically shown in FIGS. 1–3 in order to improve light output efficiency of the backlight by reflecting the light emitted from that side back through the panel for emission through the opposite side. Additionally, a pattern of optical deformities 76 may be provided on one or both sides of the backlight as schematically shown in FIGS. 1–3 in order to change the path of the light so that the internal critical angle is exceeded and a portion of the light is emitted from one or both sides of the backlight. These optical deformities 76 in the backlight BL may have the inverse shape of the optical deformities 8 of the transreflector 4 and be aligned (and if desired overlap each other) as schematically shown in FIG. 1c to increase the efficiency of light transfer from the backlight to the transreflector. Further, the region between the aligned backlight and transreflector deformities 76 and 8 may contain a refraction index matching material 79 to further increase the efficiency of such light transfer. Moreover, a transparent film, sheet or plate 77 may be attached or positioned against the side or sides of the backlight from which light is emitted as schematically shown in FIGS. 1 and 2 to further improve the uniformity of the light output distribution. For example, the film, sheet or plate may be a brightness enhancement film or a diffuser.

FIGS. 12–15 show other optical deformities 80 which may either be individual projections 81 on the respective backlight surface areas 82 or individual depressions 83 in such surface areas. In either case, each of these optical deformities 80 has a well defined shape including a reflective or refractive surface 84 that intersects the respective backlight surface area 82 at one edge 85 and has a uniform slope throughout its length for more precisely controlling the emission of light by each of the deformities. Along a peripheral edge portion 86 of each reflective/refractive surface 84 is an end wall 87 of each deformity 80 that intersects the respective panel surface area 82 at a greater included angle I than the included angle I' between the reflective/refractive surfaces 84 and the panel surface area 82 (see FIGS. 14 and 15) to minimize the projected surface area of the end walls on the panel surface area. This allows more deformities 80 to be placed on or in the panel surface areas than would otherwise be possible if the projected surface areas of the end walls 87 were substantially the same as or greater than the projected surface areas of the reflective/refractive surfaces 84.

Figure 12:
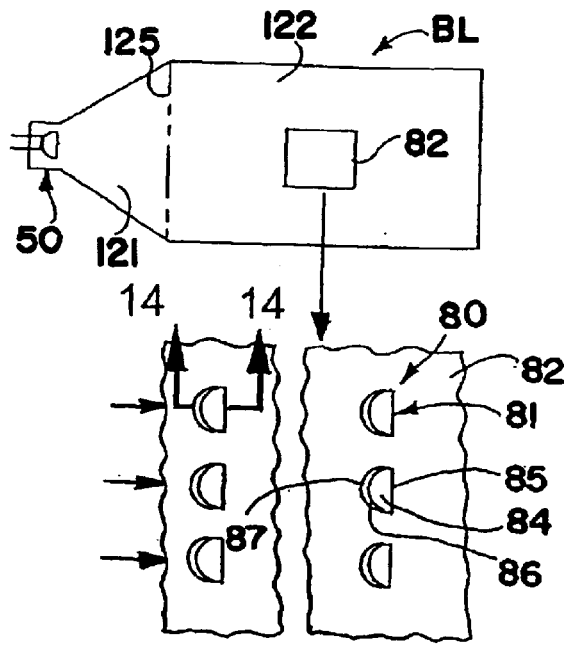
FIGS. 12 and 13 are enlarged schematic fragmentary plan views of a surface area of a backlight/light emitting panel assembly showing various forms of optical deformities in accordance with this invention formed on or in a surface of the backlight.
Figure 13:
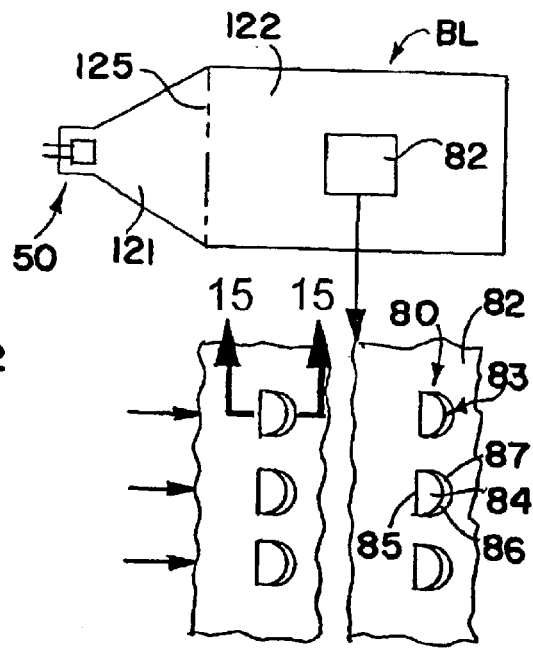
Figure 15:
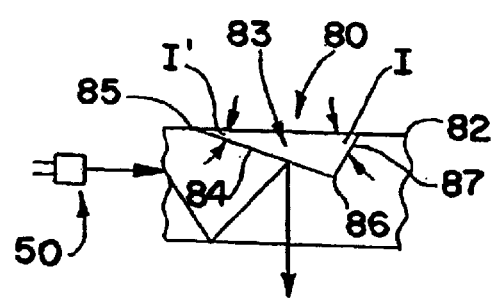
Figure 16:
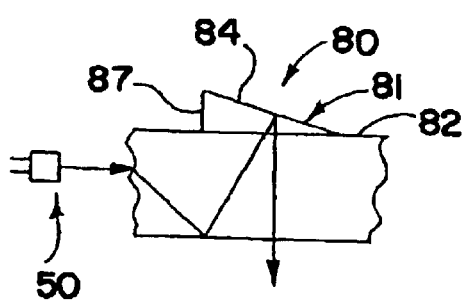
FIGS. 16 and 17 are enlarged schematic longitudinal sections through other forms of optical deformities in accordance with this invention formed on or in a surface of a backlight.
Figure 17:
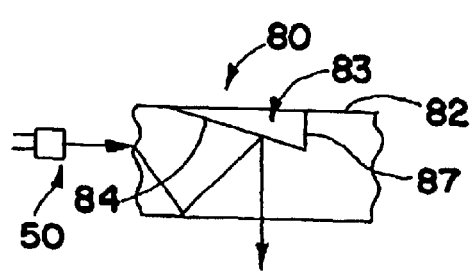

In FIGS. 12 and 13 the peripheral edge portions 86 of the reflective/refractive surfaces 84 and associated end walls 87 are curved in the transverse direction. Also in FIGS. 14 and 15 the end walls 87 of the deformities 80 are shown extending substantially perpendicular to the reflective/refractive surfaces 84 of the deformities. Alternatively, such end walls 84 may extend substantially perpendicular to the panel surface areas 82 as schematically shown in FIGS. 16 and 17. This virtually eliminates any projected surface area of the end walls 87 on the panel surface areas 82 whereby the density of the deformities on the panel surface areas may be even further increased.

Figure 18:
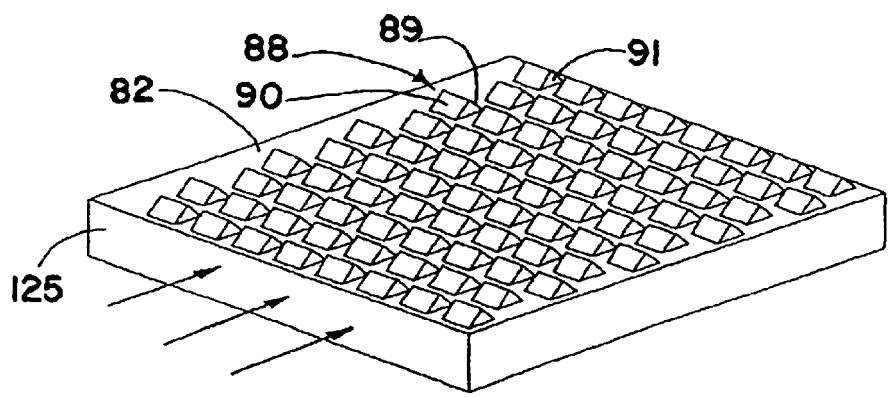
FIGS. 18–26 are enlarged schematic perspective views of backlight surface areas containing various patterns of individual optical deformities of other well defined shapes in accordance with this invention.
Figure 19:
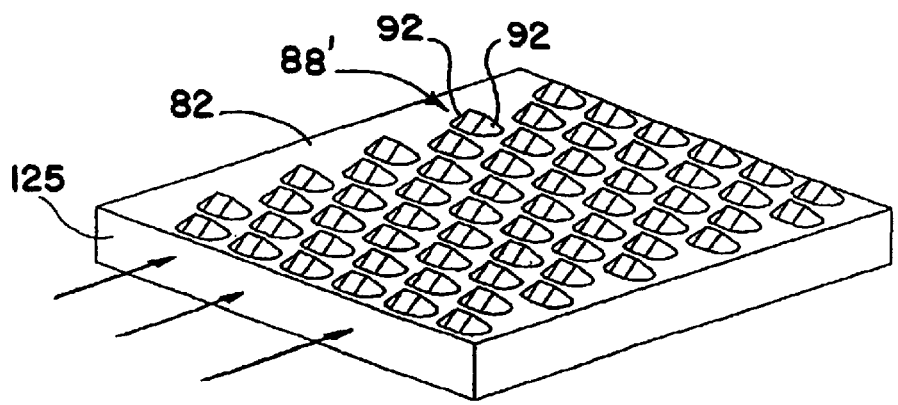

The optical deformities may also be of other well defined shapes to obtain a desired light output distribution from a panel surface area. FIG. 18 shows individual light extracting deformities 88 on a panel surface area 82 each including a generally planar, rectangular reflective/refractive surface 89 and associated end wall 90 of a uniform slope throughout their length and width and generally planar side walls 91. Alternatively, the deformities 88' may have rounded or curved side walls 92 as schematically shown in FIG. 19.

Figure 20:
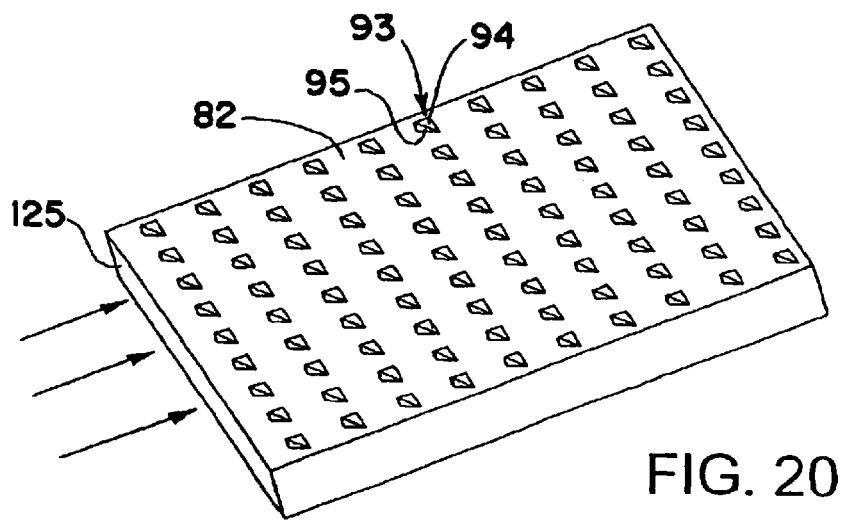
Figure 21:
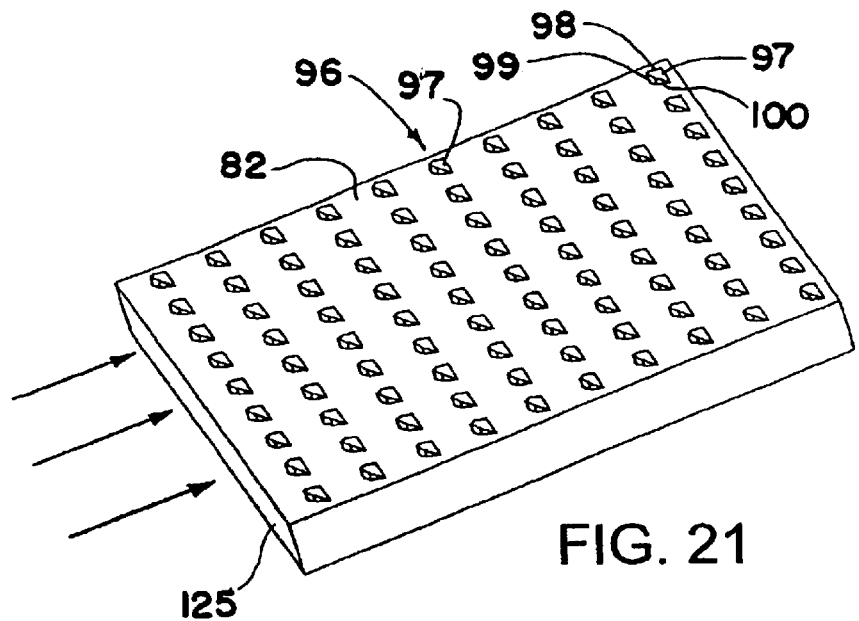

FIG. 20 shows individual light extracting deformities 93 on a panel surface area 82 each including a planar, sloping triangular shaped reflective/refractive surface 94 and associated planar, generally triangularly shaped side walls or end walls 95. FIG. 21 shows individual light extracting deformities 96 each including a planar sloping reflective/refractive surface 97 having angled peripheral edge portions 98 and associated angled end and side walls 99 and 100.

Figure 22:
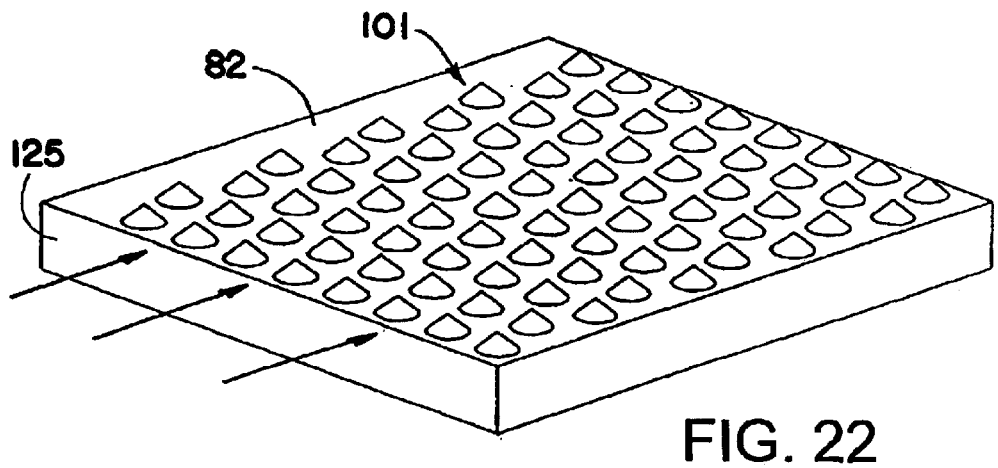
Figure 23:
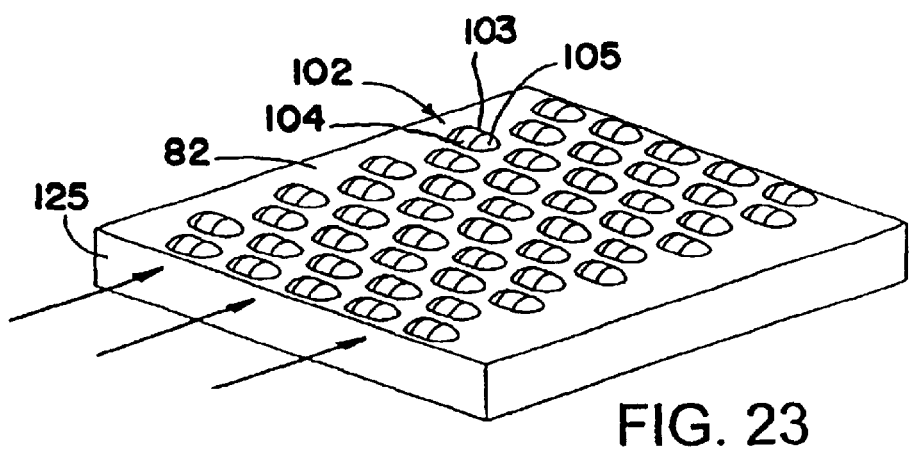

FIG. 22 shows individual light extracting deformities 101 which are generally conically shaped, whereas FIG. 23 shows individual light extracting deformities 102 each including a rounded reflective/refractive surface 103 and rounded end walls 104 and rounded or curved side walls 105 all blended together. These additional surfaces will reflect or refract other light rays impinging thereon in different directions to spread light across the backlight/panel member BL to provide a more uniform distribution of light emitted from the panel member.

Figure 14:
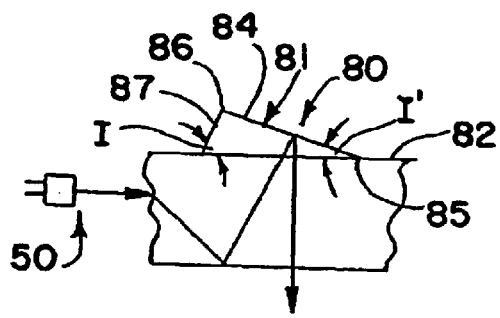
FIGS. 14 and 15 are enlarged longitudinal sections through one of the optical deformities of FIGS. 12 and 13, respectively.
Figure 24:
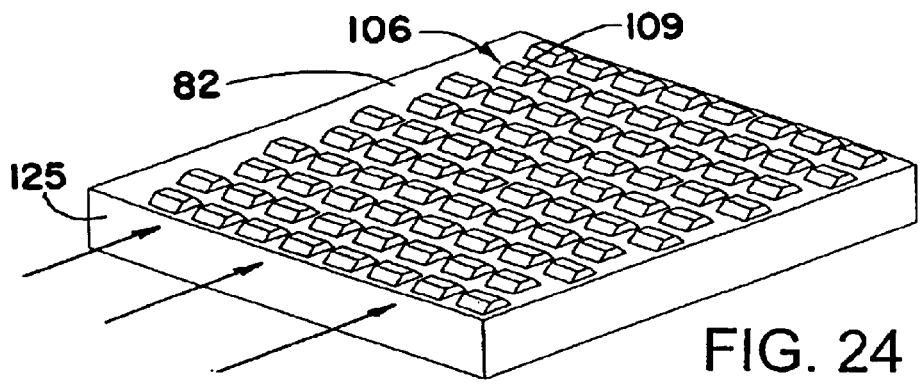
Figure 25:
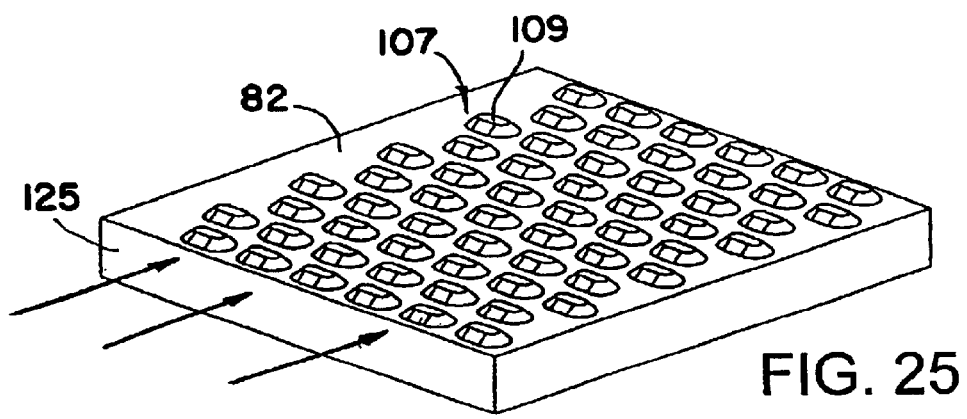
Figure 26:
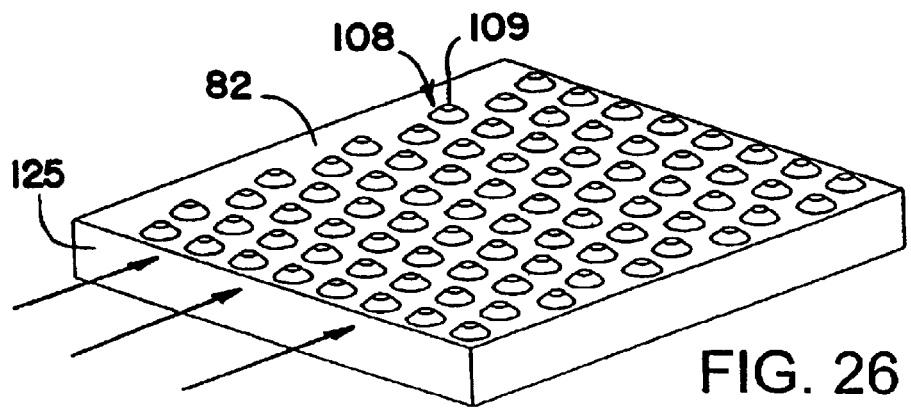
Figure 27:
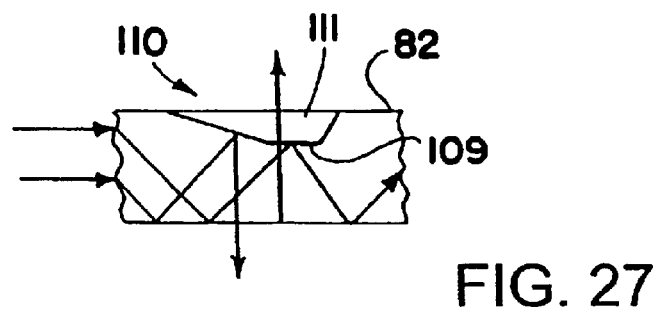
FIG. 27 is an enlarged schematic longitudinal section through another form of optical deformity in accordance with this invention formed on or in a surface of a backlight.

Regardless of the particular shape of the reflective/refractive surfaces and end and side walls of the individual deformities, such deformities may also include planar surfaces intersecting the reflective/refractive surfaces and end and/or side walls in parallel spaced relation to the panel surface areas 82. FIGS. 24–26 show deformities 106, 107 and 108 in the form of individual projections on a panel surface area having representative shapes similar to those shown in FIGS. 18, 19 and 22, respectively, except that each deformity is intersected by a planar surface 109 in parallel spaced relation to the panel surface area 82. In like manner, FIG. 27 shows one of a multitude of deformities 110 in the form of individual depressions 111 in a panel surface area 82 each intersected by a planar surface 109 in parallel spaced relation to the general planar surface of the panel surface area 82. Any light rays that impinge on such planar surfaces 109 at internal angles less than the critical angle for emission of light from the panel surface area 82 will be internally reflected by the planar surfaces 109, whereas any light rays impinging on such planar surfaces 109 at internal angles greater than the critical angle will be emitted by the planar surfaces with minimal optical discontinuities, as schematically shown in FIG. 27.

Where the deformities are projections on the panel surface area 82, the reflective/refractive surfaces extend at an angle away from the panel in a direction generally opposite to that in which the light rays from the light source 50 travel through the panel as schematically shown in FIGS. 14 and 16. Where the deformities are depressions in the panel surface area, the reflective/refractive surfaces extend at an angle into the panel in the same general direction in which the light rays from the light source 50 travel through the panel member as schematically shown in FIGS. 15 and 17.

Figure 28:
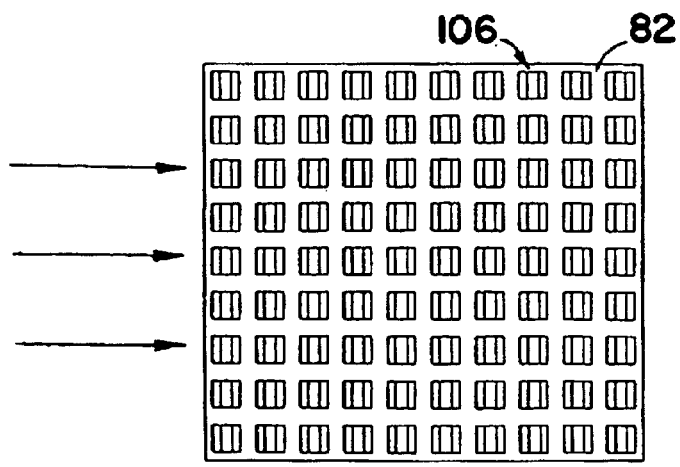
FIGS. 28 and 29 are enlarged schematic top plan views of backlight surface areas containing optical deformities similar in shape to those shown in FIGS. 24 and 25 arranged in a plurality of straight rows along the length and width of the surface areas.
Figure 29:
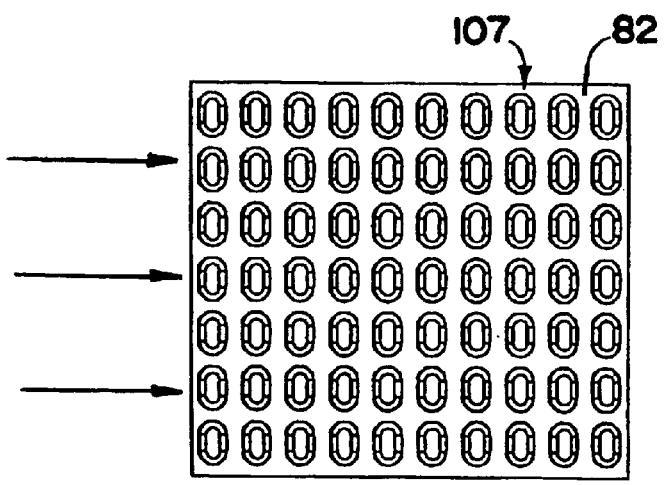
Figure 30:
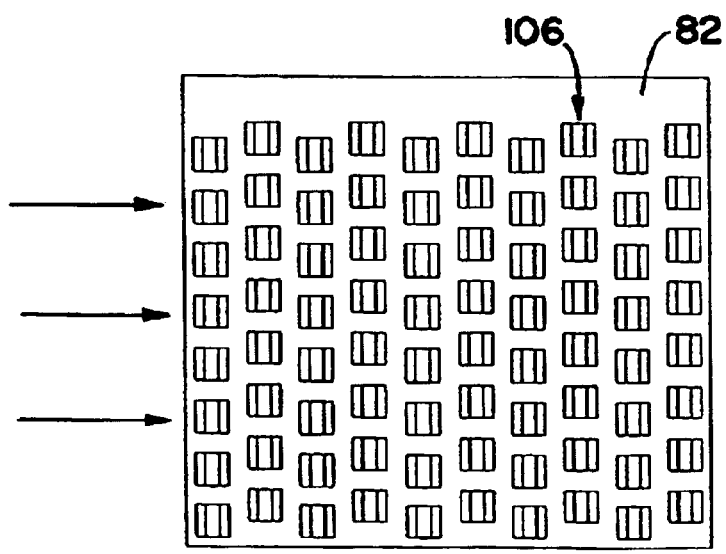
FIGS. 30 and 31 are enlarged schematic top plan views of backlight surface areas containing optical deformities also similar in shape to those shown in FIGS. 24 and 25 arranged in staggered rows along the length of the surface areas.
Figure 31:
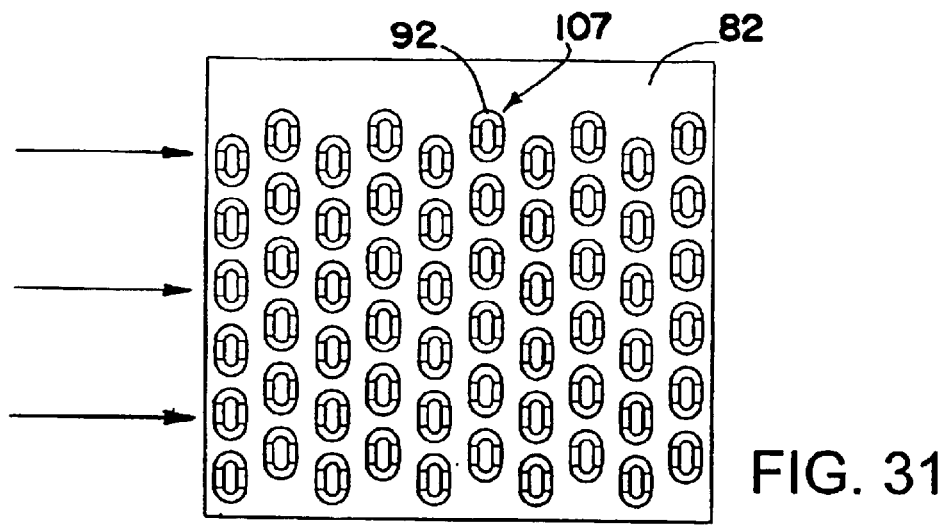

Regardless of whether the deformities are projections or depressions on or in the panel surface areas 82, the slopes of the light reflective/refractive surfaces of the deformities may be varied to cause the light rays impinging thereon to be either refracted out of the light emitting panel or reflected back through the panel and emitted out the opposite side of the panel which may be etched to diffuse the light emitted therefrom or covered by a transparent film to produce a desired effect. Also, the pattern of optical deformities on the panel surface area may be uniform or variable as desired to obtain a desired light output distribution from the panel surface areas. FIGS. 28 and 29 show deformities 106 and 107 similar in shape to those shown in FIGS. 24 and 25 arranged in a plurality of generally straight uniformly spaced apart rows along the length and width of a panel surface area 82, whereas FIGS. 30 and 31 show such deformities 106 and 107 arranged in staggered rows that overlap each other along the length of a panel surface area.

Figure 32:
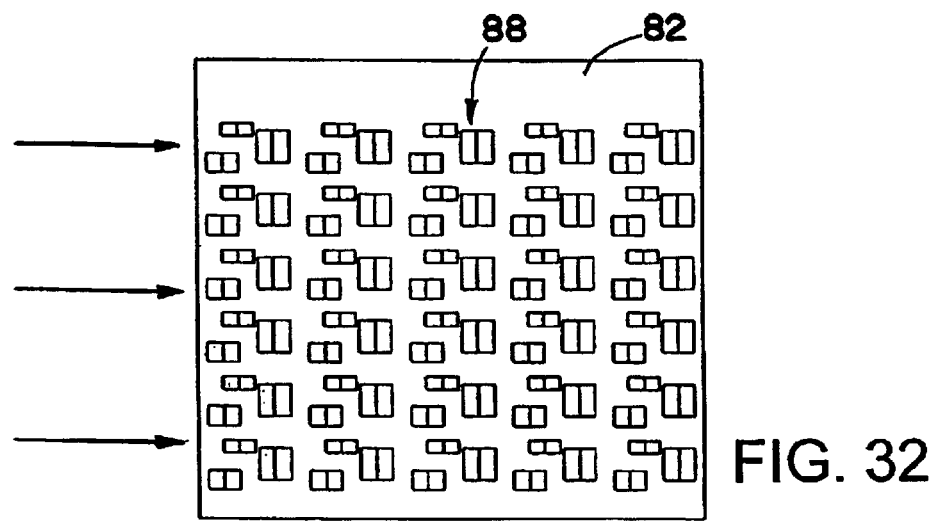
FIGS. 32 and 33 are enlarged schematic top plan views of backlight surface areas containing a random or variable pattern of clusters of different sized optical deformities on the surface areas.
Figure 33:
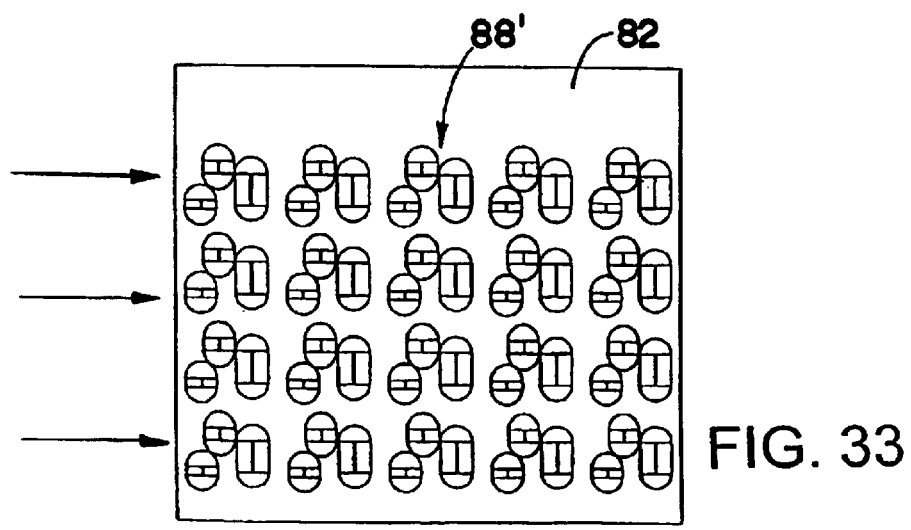
Figure 34:
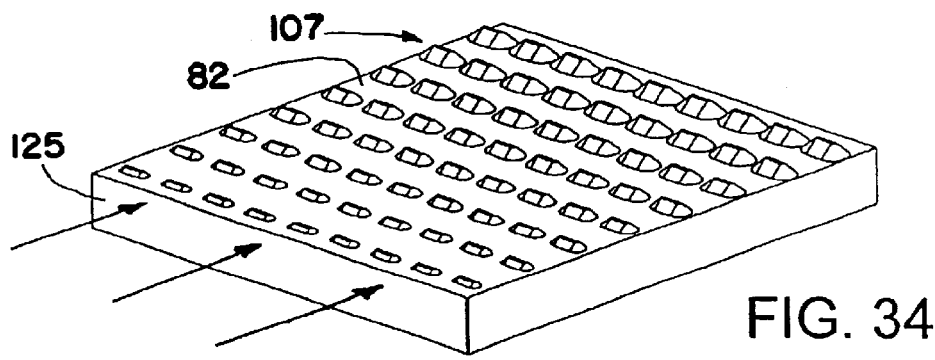
FIG. 34 is an enlarged schematic perspective view of a backlight surface area showing optical deformities in accordance with this invention increasing in size as the distance of the deformities from the light input surface increases or intensity of the light increases along the length of the surface area.

Also, the size, including the width, length and depth or height as well as the angular orientation and position of the optical deformities may vary along the length and/or width of any given panel surface area to obtain a desired light output distribution from the panel surface area. FIGS. 32 and 33 show a random or variable pattern of different size deformities 88 and 88' similar in shape to those shown in FIGS. 18 and 19, respectively, arranged in staggered rows on a panel surface area 82, whereas FIG. 34 shows deformities 107 similar in shape to those shown in FIG. 25 increasing in size as the distance of the deformities from the light source increases or intensity of the light decreases along the length and/or width of the panel surface area. The deformities 88 and 88' are shown in FIGS. 32 and 33 arranged in clusters across the panel surface, with at least some of the deformities in each cluster having a different size or shape characteristic that collectively produce an average size or shape characteristic for each of the clusters that varies across the panel surface. For example, at least some of the deformities in each of the clusters may have a different depth or height or different slope or orientation that collectively produce an average depth or height characteristic or average slope or orientation of the sloping surface that varies across the panel surface. Likewise at least some of the deformities in each of the clusters may have a different width or length that collectively produce an average width or length characteristic that varies across the panel surface. This allows one to obtain a desired size or shape characteristic beyond machinery tolerances, and also defeats moiré and interference effects.

Figure 35:
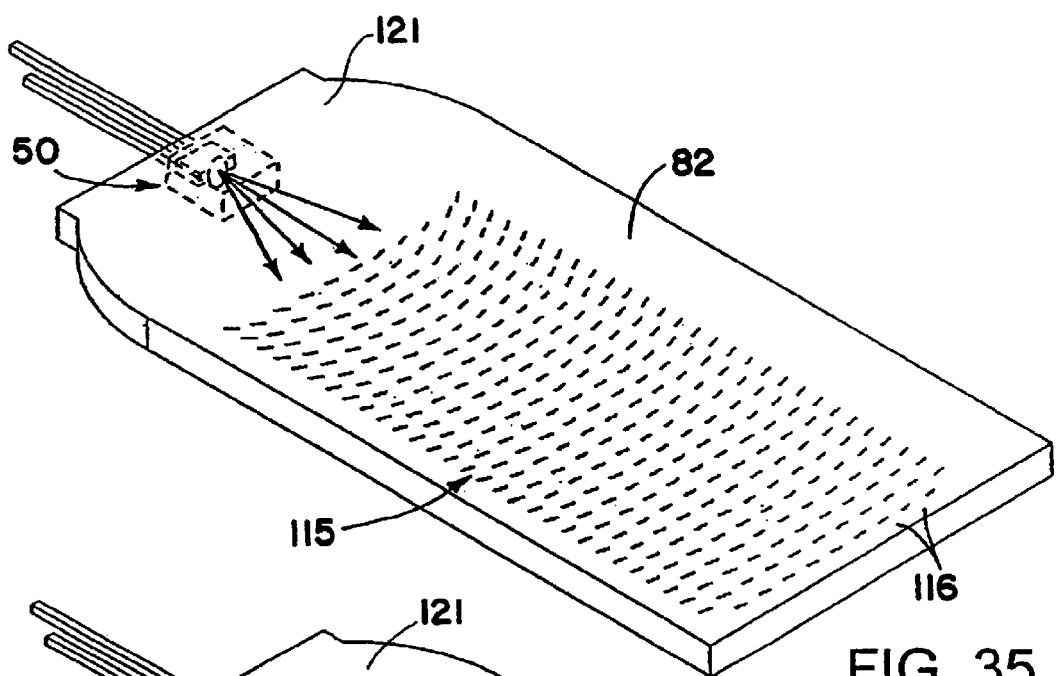
FIGS. 35 and 36 are schematic perspective views showing different angular orientations of the optical deformities along the length and width of a backlight surface area.
Figure 36:
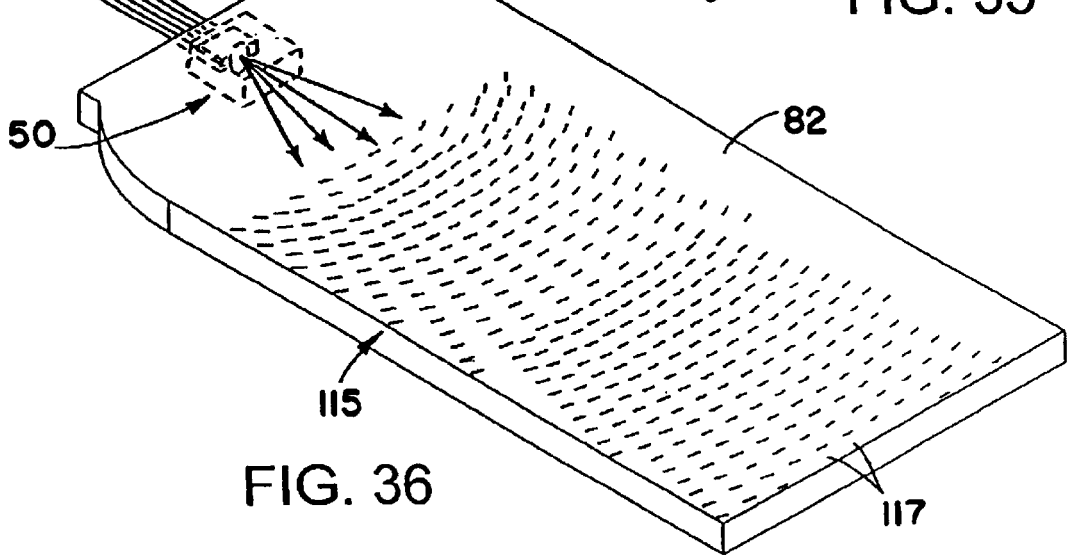

FIGS. 35 and 36 schematically show different angular orientations of optical deformities 115 of any desired shape along the length and width of a panel surface area 82. In FIG. 35 the deformities are arranged in straight rows 116 along the length of the panel surface area but the deformities in each of the rows are oriented to face the light source 50 so that all of the deformities are substantially in line with the light rays being emitted from the light source. In FIG. 36 the deformities 115 are also oriented to face the light source 50 similar to FIG. 35. In addition, the rows 117 of deformities in FIG. 36 are in substantial radial alignment with the light source 50.

FIGS. 37 and 38 schematically show how exemplary light rays 120 emitted from a focused light source 50 insert molded or cast within a light transition area 121 of a light emitting panel assembly BL in accordance with this invention are reflected during their travel through the light emitting panel member 122 until they impinge upon individual light extracting deformities 80, 107 of well defined shapes on or in a panel surface area 82 causing more of the light rays to be reflected or refracted out of one side 123 of the panel member than the other side 124. In FIG. 37 the exemplary light rays 120 are shown being reflected by the reflective/refractive surfaces 84 of the deformities 80 in the same general direction out through the same side 123 of the panel member, whereas in FIG. 38 the light rays 120 are shown being scattered in different directions within the panel member 122 by the rounded side walls 92 of the deformities 107 before the light rays are reflected/refracted out of the same side 123 of the panel member. Such a pattern of individual light extracting deformities of well defined shapes in accordance with the present invention can cause 60 to 70% or more of the light received through the input edge 125 of the panel member to be emitted from the same side of the panel member.

From the foregoing, it will be apparent that the light output distribution of the backlights of the present invention and the light input surfaces of the transreflectors of the present invention that receive incident light from the backlights may be tuned to each other so that the transreflectors will better transmit more of the light emitted by the backlights through the transreflectors.

Although the invention has been shown and described with respect to certain embodiments, it is obvious that equivalent alterations and modifications will occur to others skilled in the art upon the reading and understanding of the specification. In particular, with regard to the various functions performed by the above described components, the terms (including any reference to a "means") used to describe such components are intended to correspond, unless otherwise indicated, to any component which performs the specified function of the described component (e.g., that is functionally equivalent), even though not structurally equivalent to the disclosed component which performs the function in the herein illustrated exemplary embodiments of the invention. In addition, while a particular feature of the invention may have been disclosed with respect to only one embodiment, such feature may be combined with one or more other features of other embodiments as may be desired and advantageous for any given or particular application.

What is claimed is:

1. A transreflector comprising a transparent substrate having opposite sides, optical deformities on or in at least one of said sides, a plurality of surfaces on or in said substrate each having a reflective layer or covering for reflecting exterior light incident on the exterior one of said sides and striking said reflective surfaces, and a plurality of light transmissive surfaces on or in said substrate for transmitting exterior light incident on the exterior of the other of said sides and striking said light transmissive surfaces.

2. The transreflector of claim 1 wherein said substrate is a film or plate.

3. The transreflector of claim 1 wherein said substrate is a multilayer film.

4. The transreflector of claim 3 wherein said multilayer film is comprised of a carrier film and an ultra-violet curable layer.

5. The transreflector of claim 1 wherein said reflective surfaces and said transmissive surfaces vary in at least one of the following: size, shape, angle, and orientation.

6. The transreflector of claim 1 wherein at least some of said optical deformities overlap each other.

7. The transreflector of claim 6 wherein at least some of said optical deformities are staggered with respect to each other.

8. The transreflector of claim 6 wherein at least some of said optical deformities intersect or interlock each other.

9. The transreflector of claim 1 wherein said reflective surfaces are on or in the other side of said substrate opposite the side that receives the exterior light that is reflected by the reflective surfaces.

10. The transreflector of claim 1 wherein said reflective surfaces are on or in the same side of said substrate that receives the exterior light that is reflected by the reflective surfaces.

11. A transreflector comprising a transparent substrate having opposite sides, optical deformities on or in at least one of said sides, a plurality of reflective surfaces on or in said substrate each having a reflective layer or covering for reflecting light striking one of said sides, and a plurality of light transmissive surfaces on or in said substrate for transmitting light striking one of said sides, said optical deformities having at least two surfaces, one of said surfaces being said reflective surfaces each having said reflector layer or covering, and the other of said surfaces being said light transmissive surfaces.

12. The transreflector of claim 11 wherein said reflective layer or covering for each of said reflective surfaces is a reflective coating.

13. The transreflector of claim 11 wherein said reflective layer or covering for each of said reflective surfaces is made of metal.

14. The transreflector of claim 11 wherein said optical deformities each have a length and width substantially smaller than the length and width of said substrate and having a well defined shape.

15. The transreflector of claim 11 wherein said optical deformities run the full length or width of said substrate.

16. The transreflector of claim 15 wherein said optical deformities comprise a pattern of prismatic or lenticular surfaces.

17. A transreflector comprising a transparent substrate having opposite sides, a plurality of reflective surfaces on or in said substrate each having a reflective layer or covering for reflecting exterior light incident on the exterior of one of said sides and striking said reflective surfaces and a plurality of light transmissive surfaces on or in said substrate for transmitting exterior light incident on the exterior of the other of said sides and striking said light transmissive surfaces.

18. The transreflector of claim 17 wherein said reflective surfaces are shaped, oriented or angled to reflect a greater portion of the exterior light incident on the exterior of said one side of said substrate.

19. The transreflector of claim 17 wherein said light transmissive surfaces are shaped, oriented or angled to transmit a greater portion of the exterior light incident on the other side of said substrate.

20. The transreflector of claim 17 wherein said reflective surfaces are shaped, oriented or angled to reflect a greater portion of the exterior light incident on the exterior of said one side of said substrate and said light transmissive surfaces are shaped, oriented or angled to transmit a greater portion of the exterior light incident on the other side of said substrate.

21. The transreflector of claim 17 wherein said reflective surfaces have a substantially larger projected surface area, when projected onto a plane parallel to said substrate, than the projected surface area of said light transmissive surfaces when projected onto a plane parallel to said substrate.

22. The transreflector of claim 17 wherein said light transmissive surfaces have a substantially larger projected surface area, when projected onto a plane normal to the angle of maximum intensity of the exterior light incident on the exterior of the other side of said substrate than the projected surface area of said reflective surfaces when projected onto a plane normal to the angle of maximum intensity of the exterior light incident on the exterior of the other side of said substrate.

23. The transreflector of claim 17 wherein said light transmissive surfaces have a substantially larger projected surface area, when projected onto a plane normal to the angle of maximum intensity of the exterior light incident on the exterior of the other side of said substrate than the projected surface area of said reflective surfaces when projected onto a plane normal to the angle of maximum intensity of the exterior light incident on the exterior of the other side of said substrate, the exterior light incident on the exterior of the other side of said substrate coming from a backlight.

24. The transreflector of claim 17 wherein said reflective surfaces are substantially planar.

25. The transreflector of claim 17 wherein said reflective surfaces are curved.

26. The transreflector of claim 17 wherein said light transmissive surfaces are textured or lensed to redirect the exterior light striking said light transmissive surfaces.

27. The transreflector of claim 17 wherein said light transmissive surfaces have optical shapes on or in said light transmissive surfaces.

28. The transreflector of claim 17 wherein said light transmissive surfaces have an antireflection coating.

29. The transreflector of claim 17 wherein said reflective surfaces and said light transmissive surfaces are formed by a plurality of grooves in said substrate.

30. The transreflector of claim 17 wherein said reflective surfaces and said light transmissive surfaces are formed by a pattern of individual optical deformities on or in said substrate each having a length and width substantially smaller than the length and width of the substrate and having a well defined shape.

31. The transreflector of claim 17 wherein said reflective surfaces and said light transmissive surfaces are on or in said other side of said substrate and said one side of said substrate is shaped to redirect light.

32. The transreflector of claim 31 wherein said one side of said substrate has at least one of a texture, and optical deformities shaped to redirect the light transmitted by said transreflector.

33. The transreflector of claim 32 wherein said one side of said substrate optical deformities which comprise at least one of the following: prismatic grooves, lenticular grooves, cross grooves, and individual optical elements of deformities of well defined shape.

34. The transreflector of claim 17 wherein said reflective surfaces and said light transmissive surfaces are on or in said one side of said substrate and a pattern of individual optical deformities of well defined shape are on or in said other side of said substrate, at least some of said optical deformities vary in at least one of the following characteristics: position, size, height, density, angle, orientation, and shape.

35. A transreflector and backlight system comprising a backlight including a light emitting panel member having a panel surface that emits a light ray output distribution, and a transreflector comprised of one or more layers, said transreflector having one side in close proximity to the panel surface of the backlight, a plurality of light transmissive surfaces on or in said transreflector that transmits greater than 50% of the light ray output distribution from the panel surface incident on the exterior of the one side, and a plurality of reflective surfaces on or in said transreflector each having a reflective layer or covering that reflects more than 50% of ambient light incident on exterior of the other side.

36. The system of claim 35 further comprising a display in close proximity to the other side of the transreflector for receiving ambient light reflected by the transreflector and light from the backlight transmitted by the transreflector.

37. The system of claim 36 wherein the display is a liquid crystal display.

38. A transreflector and backlight system comprising a backlight including a light emitting panel member having at least one input edge for receiving light from a light source and at least one panel surface for emitting light, and a transreflector for transmitting light emitted by said panel surface incident on the exterior of one side of said transreflector and for reflecting ambient light incident on the exterior of the opposite side of said transreflector, at least one of said sides of said transreflector having optical deformities, a plurality of reflective surfaces on or in said transreflector each having a reflective layer or covering for reflecting ambient light incident on the exterior of said opposite side of said transreflector, and a plurality of light transmissive surfaces on or in said transreflector for transmitting light emitted by said panel surface incident on the exterior of said one side of said transreflector.

39. The system of claim 38 wherein said deformities have at least two surfaces, one of said surfaces being said reflective surfaces each having said reflective layer or covering and the other of said surfaces being said light transmissive surfaces.

40. A transreflector and backlight system comprising a backlight including a light emitting panel member having at least one input edge for receiving light from a light source and at least one panel surface for emitting light, and a transreflector for transmitting light emitted by said panel surface incident on the exterior of one side of said transreflector and for reflecting ambient light incident on the exterior of the opposite side of said transreflector, one or the other of said sides of said transreflector having a plurality of reflective surfaces each having a reflective layer or covering for reflecting the ambient light incident on the exterior of said opposite side of said transreflector and a plurality of light transmissive surfaces for transmitting the light emitted by said panel surface incident on the exterior of said one side of said transreflector.

41. The system of claim 40 wherein said reflective surfaces are shaped, oriented or angled to reflect more than 50% of the light incident on the exterior of said one side of said transreflector.

42. The system of claim 40 wherein said light transmissive surfaces are shaped, oriented or angled to transmit more than 50% of the light incident on the exterior of the other side of said transreflector.

43. The system of claim 40 wherein said reflective surfaces are shaped, oriented or angled to reflect more than 50% of the light incident on the exterior of said one side of said transreflector and said light transmissive surfaces are shaped, oriented or angled to transmit more than 50% of the light incident on the exterior the other side of said transreflector.

44. The system of claim 40 wherein said panel member has a pattern of individual optical deformities for producing a particular light output distribution from said panel surface that is tuned to the side of the transreflector that receives incident light emitted by said panel surface such that said transreflector transmits a greater portion of the light emitted by said panel surface.

45. The system of claim 40 wherein said reflective surfaces and said light transmissive surfaces are formed in or on said opposite side of said transreflector, and said one side of said transreflector has optical deformities that transmit the incident light emitted from said panel surface and direct the light to said light transmissive surfaces in or on said opposite side of said transreflector.

46. The system of claim 45 wherein said optical deformities which comprise at least one of the following: prismatic grooves, lenticular grooves, cross grooves, and individual optical deformities of well defined shape.

47. The system of claim 40 wherein said reflective surfaces and said light transmissive surfaces are in or on said one side of said transreflector, and said opposite side of said transreflector has optical deformities for redirecting the light exiting from said opposite side more toward the normal relative to said opposite side of said transreflector.

48. The system of claim 47 wherein said optical deformities comprise a pattern of prismatic surfaces.

49. The system of claim 47 wherein said optical deformities comprise a pattern of individual optical deformities each having a well defined shape.

50. The system of claim 40 wherein said reflective surfaces and said light transmissive surfaces are in or on said one side of said transreflector, and said opposite side of said transreflector has at least one of a texture, chemical etch, laser etch, and optical deformities shaped to redirect the light transmitted by said transreflector.

51. The system of claim 50 wherein said opposite side of said transreflector has said optical deformities which comprise at least one of the following: prismatic grooves, lenticular grooves, cross grooves and individual optical deformities of well defined shape.

52. The system of claim 40 wherein said panel member has a pattern of individual optical deformities for producing a particular light output distribution from said panel surface, at least some of said deformities of said panel member having a length and width that is substantially smaller than the length and width of said panel member and a well defined shape including at least one sloping surface for reflecting or refracting light impinging thereon out of said panel surface.

53. The system of claim 52 wherein said sloping surface of at least some of said deformities of said panel member is oriented to face an optically coupled area of said input edge across said panel member.

54. The system of claim 52 wherein the area of said sloping surface of at least some of said deformities of said panel member varies across said panel member to attain a desired light output distribution from said panel surface.

55. The system of claim 52 wherein said sloping surface of at least some of said deformities of said panel member is a planar surface, further comprising at least one light source optically coupled to said input edge, said planar surface of the respective deformities of said panel member being oriented across said panel member to face an area of said input edge to which the light source is optically coupled.

56. The system of claim 52 further comprising a display having one side in close proximity to a side of said transreflector facing away from said panel member.

57. The system of claim 56 wherein said display is signage, a liquid crystal display, or a membrane switch.

58. The system of claim 57 wherein said display is a liquid crystal display and said pattern of said optical deformities of said panel member is varied such that the spacing of said optical deformities of said panel member does not cause interference with any pixel spacing of the liquid crystal display.

59. A transreflector comprising a transparent film or substrate of one or more layers, a plurality of light transmissive surfaces on or in said film or substrate that transmit greater than 50% of exterior light incident on the exterior of one side of said film or substrate, and a plurality of reflective surfaces on or in said film or substrate each having a reflective layer or covering that reflects more than 50% of a different exterior light incident on the exterior of the other side of said film or substrate that has a different light ray angle distribution than the light ray angle distribution of the exterior light incident on the exterior of the one side.

* * * * *

UNITED STATES PATENT AND TRADEMARK OFFICE
CERTIFICATE OF CORRECTION

PATENT NO. : 6,827,456 B2
DATED : December 7, 2004
INVENTOR(S) : Jeffery R. Parker et al.

It is certified that error appears in the above-identified patent and that said Letters Patent is hereby corrected as shown below:

<u>Column 18,</u>
Line 27, -- has said -- should be inserted before "optical".
Line 49, -- the -- should be inserted before "exterior".

<u>Column 19,</u>
Line 56, "which" should be deleted.

Signed and Sealed this

First Day of March, 2005

JON W. DUDAS
*Director of the United States Patent and Trademark Office*